United States Patent
Diec et al.

(10) Patent No.: US 6,607,733 B1
(45) Date of Patent: Aug. 19, 2003

(54) COSMETIC OR DERMATOLOGICAL GELS BASED ON MICROEMULSIONS

(75) Inventors: Khiet Hien Diec, Hamburg (DE); Heinrich Gersbarlag, Kummerfeld (DE); Manfred Klier, Aumühle (DE); Jörg Schreiber, Hamburg (DE); Florian Wolf, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 08/930,404

(22) PCT Filed: Mar. 14, 1996

(86) PCT No.: PCT/EP96/01088

§ 371 (c)(1),
(2), (4) Date: Jan. 20, 1998

(87) PCT Pub. No.: WO96/28132

PCT Pub. Date: Sep. 19, 1996

(30) Foreign Application Priority Data

Mar. 15, 1995 (DE) .......................... 195 09 079

(51) Int. Cl.$^7$ .............................. A61K 6/00; A61K 7/00
(52) U.S. Cl. .................. 424/401; 514/941; 514/944
(58) Field of Search ................ 424/401, 455; 514/944, 941

(56) References Cited

U.S. PATENT DOCUMENTS

| 4,477,375 | A | * | 10/1984 | Grollier ....................... 252/542 |
| 5,077,040 | A | * | 12/1991 | Bergmann et al. ............. 424/70 |
| 5,156,766 | A | * | 10/1992 | Behan et al. ................ 252/312 |
| 5,167,281 | A | * | 12/1992 | Kalfoglou .................... 166/275 |
| 5,334,581 | A | * | 8/1994 | Behan et al. .................. 512/2 |
| 5,399,652 | A | * | 3/1995 | Bindl et al. .................... 528/26 |
| 5,426,182 | A | * | 6/1995 | Jenkins et al. ................. 536/54 |
| 5,905,062 | A | * | 5/1999 | Elliott et al. ................. 510/124 |

OTHER PUBLICATIONS

Happy Household and Personal Products, vol.30, pp.58–64, Feb. 1993.*

* cited by examiner

Primary Examiner—Michael G. Hartley
(74) Attorney, Agent, or Firm—Norris McLaughlin & Marcus

(57) ABSTRACT

Microemulsion gels based on microemulsions of the oil-in-water type in which the droplets of the discontinuous oily phase are joined to one another by one or more crosslinking substances, the molecules of which are distinguished by at least one hydrophilic region, which has an extension which is capable of bridging the customary distance between the microemulsion droplets, and by at least one hydrophobic region, which is capable of entering into a hydrophobic interaction with the microemulsion droplets.

9 Claims, 3 Drawing Sheets

W/O Emulsions

O/W Emulsions

% by weight of aqueous phase

COSMETIC OR DERMATOLOGICAL GELS BASED ON MICROEMULSIONS

This application is a 371 of PCT/EP96/01088, which was filed on Mar. 14, 1996.

BACKGROUND OF THE INVENTION

The present invention relates to cosmetic or dermatological gels based-on microemulsions, in particular such gels for cosmetic and dermatological formulations. As a particular embodiment, the present invention relates to cosmetic or dermatological gels based on microemulsions of the oil-in-water type, processes for their preparation and their use for cosmetic and medical purposes.

Cosmetic skin care is primarily to be understood as meaning that the natural function of the skin as a barrier against environmental influences (for example dirt, chemicals and microorganisms) and against the loss of endogenous substances (for example water, natural fats and electrolytes) is intensified or re-established.

If this function is impaired, increased absorption of toxic or allergenic substances or attack by microorganisms and as a consequence toxic or allergic skin reactions may occur.

The aim of skin care is furthermore to compensate the loss of fats and water from the skin caused by daily washing. This is important particularly if the natural capacity for regeneration is not adequate. Skin-care products should furthermore protect against environmental influences, in particular against the sun and wind, and delay ageing of the skin.

Medical topical compositions as a rule comprise one or more medicaments in an active concentration. For simplicity, reference is made to the legal provisions of the Federal Republic of Germany (for example cosmetics legislation, legislation on foodstuffs and medicaments) for a clear distinction between cosmetic and medical use and corresponding products.

Gels are customary cosmetic and dermatological formulation forms which have become more and more widespread particularly in recent times.

In the technical sense, gels are understood as meaning: relatively dimensionally stable, easily deformable disperse systems of at least two components, which as a rule comprise a—usually solid—colloidally divided substance of long-chain molecular grouping (for example gelatin, silicic acid or polysaccharides) as the matrix-forming phase and a liquid dispersing agent (for example water). The colloidally divided substance is often called a thickener or gelling agent. It forms a three-dimensional network in the dispersing agent, it being possible for individual particles present in colloidal form to be linked to one another more or less firmly via electrostatic interaction. The dispersing agent, which surrounds the network, is distinguished by electrostatic affinity for the gelling agent, i.e. a predominantly polar (in particular: hydrophilic) gelling agent preferably gels a polar dispersing agent (in particular: water), whereas a predominantly non-polar gelling agent preferably gels non-polar dispersing agents.

Strong electrostatic interactions, which are realized, for example, in hydrogen bridge bonds between the gelling agent and dispersing agent, but also between dispersing agent molecules with one another, can lead to a high degree of crosslinking of the dispersing agent as well. Hydrogels can comprise water to the extent of almost 100% (alongside, for example, about 0.2–1.0% of a gelling agent), and at the same time have an entirely solid consistency. The water content is present here in ice-like structural elements, so that gels entirely justify the origin of their name [from lat. "gelatum"="frozen" by the alchemistic term "gelatina" (16th century) for the modern term "gelatin"].

Lipogels and oleogels (of waxes, fats and fatty oils) as well as carbogels (from paraffin or petrolatum) are furthermore also customary in cosmetic and pharmaceutical galenics. In practice, a distinction is made between oleogels, which are in practically anhydrous form, and hydrogels, which are practically fat-free. Gels are usually transparent. In cosmetic and pharmaceutical galenics, gels are as a general rule distinguished by a semi-solid, often free-flowing consistency.

In simple emulsions, in the one phase, finely dispersed droplets of the second phase (water droplets in W/O or lipid vesicles in O/W emulsions) enclosed by an emulsifier shell are present. The droplet diameters of the usual emulsions are in the range from about 1 $\mu$m to about 50 $\mu$m. Without further colouring additives, such "macroemulsions" are milky white in colour and opaque. Finer "macroemulsions", the droplet diameters of which are in the range from about $10^{-1}$ $\mu$m to about 1 $\mu$m, again without colouring additives, are bluish-white in colour and non-transparent.

It is the property of micellar and molecular solutions having particle diameters of less than about $10^{-2}$ $\mu$m to appear clear and transparent.

The droplet diameter of transparent or translucent microemulsions, on the other hand, is in the range from about $10^{-2}$ $\mu$m to about $10^{-1}$ $\mu$m. Such microemulsions usually have a low viscosity. The viscosity of many microemulsions of the O/W type is comparable to that of water.

So-called surfactant gels are furthermore customary formulations of the prior art. These are understood as being systems which, in addition to water, have a high concentration of emulsifiers, typically more than about 25% by weight, based on the total composition. If oil components are solubilized in these surfactant gels, which is their technical name, microemulsion gels, which are also called "ringing gels" are obtained. Cosmetically more elegant microemulsion gels can be obtained by addition of nonionic emulsifiers, for example alkyl poly-glycosides. Here also, the high content of emulsifiers is a disadvantage.

An advantage of microemulsion gels is that active compounds can be present in finely disperse form in the disperse phase. Another advantage is that, because of their low viscosity, they can be sprayed. When microemulsions are used as cosmetics, corresponding products are distinguished by a high cosmetic elegance.

It is known per se to link the droplets of a low-viscosity, in particular thinly liquid microemulsion with crosslinking substances with one another, in order to obtain the three-dimensional network of a gel in this manner.

Chain-like, hydrophilic molecules which contain a hydrophobic radical on each of the two chain ends are described in Nachr. Chem. Techn. Lab. 43 (1995) No. 1, page 9 et seq for crosslinking microemulsion droplets. Those hydrophobic radicals are immersed in the microemulsion droplets, the hydrophilic chain regions being in the continuous aqueous phase. In the strict sense, it is certainly not necessary for the hydrophobic radicals to be "immersed". In individual cases, it can also be entirely sufficient if the hydrophobic radicals come into contact with. the surface of the microemulsion droplets by hydrophobic interaction and remain stuck to these more or less firmly.

Crosslinking agents which are mentioned in the above reference are polyoxyethylene glycols with oleyl groups as hydrophobic end groups.

This principle is illustrated in FIG. 5: the microemulsion droplets of an O/W microemulsion, which are shown as shaded circles, are joined to one another by the crosslinking agent molecules shown as lines, these carrying hydrophobic radicals, symbolized by rectangles, at both ends. It can be seen that in principle an emulsion droplet can also accommodate several hydrophobic radicals, as a result of which a higher degree of crosslinking and three-dimensionality of the network can be ensured.

A disadvantage of microemulsions, and therefore also of the microemulsion gels of the prior art, is that a high content of one or more emulsifiers must always be employed, since the low droplet size results in a high interface between the phases, which as a rule must be stabilized by emulsifiers.

The use of the customary cosmetic emulsifiers is indeed acceptable per se. Nevertheless, emulsifiers, like any chemical substance in the end, can cause allergic reactions or reactions based on hypersensitivity of the user in an individual case.

It is thus known that particular photodermatoses are induced by certain emulsifiers, and also by various fats, and simultaneously exposure to sunlight. Such photodermatoses are also called "Majorca acne". An object of the present invention was therefore to develop sunscreen products.

As particular embodiments, the present invention thus relates to cosmetic and dermatological light protection formulations, in particular skin-care cosmetic and dermatological light protection formulations.

The damaging effect of the ultraviolet part of solar radiation on the skin is generally known. While rays having a wavelength of less than 290 nm (the so-called UVC range) are absorbed by the ozone layer in the Earth's atmosphere, rays in the range between 290 nm and 320 nm, the so-called UVB range, cause erythema, simple sunburn or even actual burns of greater or lesser severity.

The narrower range around 308 nm is seen as the erythema activity maximum of sunlight.

Numerous compounds are known for protection against UVB radiation, these usually being derivatives of 3-benzylidenecamphor, of 4-aminobenzoic acid, of cinnamic acid, of salicylic acid, of benzophenone and also of 2-phenylbenzimidazole.

For the range between about 320 nm and about 400 nm, the so-called UVA range, it is also important to have available filter substances, since the rays thereof can also cause damage. It has thus been proved that UVA radiation leads to damage to the elastic and collagenic fibres of connective tissue, which makes the skin age prematurely, and that it has to be regarded as a cause of numerous phototoxic and photoallergic reactions. The damaging effect of UVB radiation can be intensified by UVA radiation.

However, UV radiation can also lead to photo-chemical reactions, the photochemical reaction products then intervening in the skin metabolism.

To prevent these reactions, antioxidants and/or agents which trap free radicals can additionally be incorporated into the cosmetic or dermatological formulations.

Most inorganic pigments, which are known to be used in cosmetics for protecting the skin against UV rays, are UV absorbers or UV reflectors. These pigments are oxides of titanium, zinc, iron, zirconium, silicon, manganese, aluminium and cerium, and mixtures thereof, as well as modifications.

Microemulsion gels are also suitable for other cosmetic dermatological uses, for example deodorants, so that in a particular embodiment, the present invention relates to microemulsion gels as a base for cosmetic deodorants.

Cosmetic deodorants serve to eliminate body odour, which develops when fresh perspiration, which is odourless per se, is decomposed by microorganisms. The customary cosmetic deodorants are based on various action principles.

In so-called antiperspirants, the formation of perspiration can be reduced by astringents—chiefly aluminium salts, such as aluminium hydroxy chloride (hydrated aluminium chloride).

By using antimicrobial substances in cosmetic deodorants, the bacterial flora on the skin can be reduced. In the ideal case, only the odour-causing microorganisms should be effectively reduced here. The flow of perspiration itself is not influenced as a result, and in the ideal case only the microbial decomposition of the perspiration is temporarily stopped.

Combination of astringents with antimicrobially active substances in one and the same composition is also customary.

Deodorants should meet the following conditions:
1) They should cause reliable deodorization.
2) The natural biological processes of the skin must not be impaired by the deodorants.
3) The deodorants must be harmless in the event of an overdose or if used other than as specified.
4) They should not become concentrated on the skin after repeated use.
5) They should be easy to incorporate into customary cosmetic formulations.

Both liquid deodorants, for example aerosol sprays, roll-ons and the like, and solid formulations, for example deodorant sticks, powders, powder sprays, intimate cleansing compositions and the like, are known and customary.

The use of microemulsions as a base for formulations having a deodorizing or antiperspirant action is also known. Their relatively high content of emulsifiers with the disadvantages described has to date been a poor state of affairs which was to be remedied.

Another object of the present invention was thus to develop formulations which are suitable as a base for cosmetic deodorants or antiperspirants and do not have the disadvantages of the prior art.

It was furthermore an object of the invention to develop cosmetic bases for cosmetic deodorants which are distinguished by a good skin tolerability.

It was furthermore an object of the present invention to provide products based on microemulsion gels with the broadest possible diversity of uses. For example, bases for formulation forms such as cleansing emulsions, face- and body-care formulations, and also distinctly medical/pharmaceutical presentation forms, for example formulations against acne and other skin manifestations, were to be provided.

In a particular embodiment, the invention therefore relates to cleansing emulsions, in particular facial cleansing emulsions, preferably make-up removers, for example eye make-up removers.

Such formulations are known per se. They are usually mixtures of cosmetic oils or aqueous formulations of surface-active substances, the function of which is to solubilize the contamination or the make-up particles and remove them from the skin.

Waterproof eye make-up, for example mascara, can be removed satisfactorily with water-based make-up removers only with special surfactants. However, these surfactants often have only a limited physiological tolerability. When such substances come into contact with the mucous membrane, in particular the mucous membrane of the eye, these substances lead to irritation, which manifests itself, for example, in a reddening of the eyes. Reactions of this type are typical of surfactant-containing products.

An object of the present invention is consequently to provide a remedy for such problems.

In another embodiment, the present invention relates to hair cosmetics formulations. In particular, the present invention relates to hair cosmetics formulations for care of the hair and the scalp. In a preferred embodiment, the present invention relates to formulations which serve to strengthen the individual hairs and/or to impart hold and fullness to the hairstyle overall.

Roughly speaking, human hair can be divided into the living part, the hair root, and the dead part, the hair shaft. The hair shaft in turn comprises the medulla, which nevertheless through evolution has become insignificant for modern man and has receded, and in the case of thin hair is often absent entirely, and furthermore the cortex which surrounds the medulla and the cuticula which encloses the entirety of the medulla and cortex.

The cuticula in particular, but also the keratinous region between the cuticula and cortex, as the outer shell of the hair, are exposed to particular demands due to environmental influences, due to combing and brushing, and also due to hair treatment, in particular colouring of the hair and deforming of the hair, for example permanent wave processes.

When exposed to particularly aggressive demands, for example bleaching with oxidizing agents, such as hydrogen peroxide, in which the pigments distributed in the cortex are destroyed by oxidation, the inside of the hair can also be affected. If human hair is to be coloured permanently, in practice only oxidizing hair-colouring processes are possible. In the case of oxidative colouring of the hair, the dyestuff chromophores are formed by reaction of precursors (phenols, aminophenols and less frequently also diamines) and bases (usually p-phenylenediamine) with the oxidizing agent, usually hydrogen peroxide. Hydrogen peroxide concentrations of about 6% are usually used for this.

The process is usually based on a bleaching action by the hydrogen peroxide taking place, in addition to the colouring action. In human hair coloured by oxidation, as with bleached hair, microscopic holes are detectable at the points where melanin granules were present. It is a fact that the oxidizing agent hydrogen peroxide reacts not only with the colour precursors but also with the hair substance and as a result under certain circumstances can cause damage to the hair.

Washing the hair with aggressive surfactants can also make demands on the hair, and at least reduce its appearance or the appearance of the hairstyle overall. For example, certain water-soluble hair constituents (for example urea, uric acid, xanthine, keratin, glycogen, citric acid and lactic acid) can be leached out by washing the hair.

For these reasons, in some cases hair-care cosmetics which are intended to be rinsed out of the hair again after their action and in some cases those which are to remain on the hair have been used for a relatively long time. The latter can be formulated such that they not only care for the individual hair, but also improve the appearance of the hairstyle overall, for example by imparting to the hair more fullness, fixing the hairstyle over a longer period of time or improving its ease of styling.

For example, the combability of hair can be improved decisively by quaternary ammonium compounds. Such compounds are absorbed onto the hair and are often still detectable on the hair after the hair has been washed several times.

However, the prior art has lacked active compounds and formulations which satisfactorily provide care for damaged hair. Formulations which should give the hairstyle fullness have also often proved to be inadequate, or at least they were unsuitable for use as hair-care formulations. Formulations of the prior art which fix the hairstyle as a rule comprise, for example, viscous constituents, which run the risk of giving rise to a feeling of tackiness, which often has to be compensated by skilful formulation.

An object was therefore to remedy the disadvantages of the prior art.

A particular object of the present invention was to provide gelatinous formulations based on finely dispersed systems of the oil-in-water type with the lowest possible emulsifier content which do not have the dis-advantages of the prior art and which can have the most diverse cosmetic and/or dermatological applications, for example the uses described above. Another object of the invention was to enrich the limited range of gelatinous formulations based on finely dispersed systems of the oil-in-water type of the prior art.

It is known per se that hydrophilic emulsifiers, that is to say polyethoxylated and polypropoxylated emulsifiers, change their solubility properties from water-soluble to fat-soluble as the temperature increases. A characteristic of the hydrophilicity of a given emulsifier is its HLB value.

The definition of the HLB value for polyol fatty acid esters is given by the formula I $$HLB=20*(1-S/A)$$

For a group of emulsifiers, the hydrophilic content of which comprises only ethylene oxide units, the formula II applies $$HLB=E/5$$

wherein S=saponification number of the ester,

A=acid number of the acid recovered

E=proportion by weight of ethylene oxide (in %) in the total molecule.

Emulsifiers having HLB values of 6–8 are in general W/O emulsifiers, and those having HLB values of 8–18 are in general O/W emulsifiers.

Literature: "Kosmetik—Entwicklung, Herstellung und Anwendung kosmetischer Mittel" [Cosmetics—development, preparation and use of cosmetic agents]; W. Umbach (Editor), Georg Thieme Verlag 1988.

The temperature range in which the emulsifiers change their solubility is called the phase inversion temperature range. Within this specification, the abbreviation "PIT" will also be used for the phase inversion temperature range.

As is known, the change in these solubility properties manifests itself in that a mixture of water, oil and O/W emulsifiers which gives an O/W emulsion after stirring below the PIT when brought to a temperature above the PIT, typically about 70–90° C., can pass through the state of a microemulsion as an intermediate stage, to finally give a W/O emulsion above the PIT. If this emulsion is cooled, an O/W emulsion is obtained again, but this has a droplet size of up to 200 nm, and is in the region here between a microemulsion and a fine macroemulsion.

However, microemulsions of the prior art prepared in such a manner have the disadvantage that firstly the droplet size is still quite high, and that the emulsion is opaque white to bluish at room temperature and/or a high proportion of one or more emulsifiers is still necessary.

Another disadvantage is that although microemulsions prepared in such a manner are practically transparent at a high temperature, that is to say, for example, in the PIT, they become non-transparent again on falling to room temperature. Gels based on such microemulsions are thus at best unattractive, but also have disadvantages from the technical, galenical and cosmetic point of view.

The object was therefore also to remedy this poor state of affairs.

SUMMARY OF THE INVENTION

Astonishingly, all the objects on which the invention is based are achieved by microemulsion gels, (a) based on microemulsions of the oil-in-water type, which comprise
an oily phase, which is essentially composed of constituents of low volatility, and an aqueous phase
comprising: one or more polyethoxylated O/W emulsifiers and/or one or more polypropoxylated O/W emulsifiers and/or one or more polyethoxylated and polypropoxylated O/W emulsifiers, if desired furthermore comprising one or more W/O emulsifiers
having an emulsifier content of less than 20% by weight, based on the total weight of the emulsion,
obtainable by bringing a mixture of the base components, comprising the aqueous phase, the oily phase, one or more of the O/W emulsifiers according to the invention, if desired one or more W/O emulsifiers, and if desired further auxiliaries, additives and/or active compounds, to a temperature within or above the phase inversion temperature range, and thereafter cooling it to room temperature;

(b) in which the droplets of the discontinuous oily phase are joined to one another by one or more crosslinking substances, the molecules of which are distinguished by at least one hydrophilic region, which has an extension which is capable of bridging the distance between the microemulsion droplets, and by at least one hydrophobic region, which is capable of entering into a hydrophobic interaction with the microemulsion droplets.

BRIEF DESCRIPTION OF THE DRAWINGS

The invention will now be described in greater detail with reference to the drawings, wherein.

DETAILED DESCRIPTION OF THE INVENTION

Figure 1:
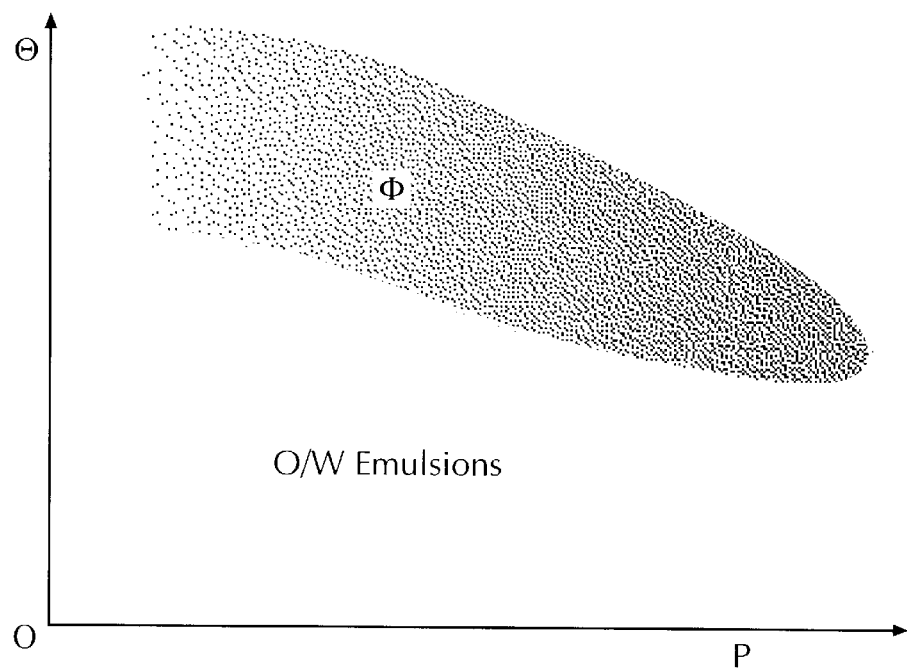
FIG. 1 is a graph wherein the variable parameter (P) is plotted against the temperature(Θ).

It is equally advantageous here if the crosslinking substance, also called a thickener in the context of the present description, forms an independent gel network in which the microemulsion droplets are then held firmly by the hydrophobic interaction (so-called associated thickeners are then present), or if the network is held together by the crosslinking with the microemulsion droplets in the junctions of the network.

The crosslinking substances used according to the invention as a rule follow structural diagrams as follows:

  (1)

  (2)

  (3)

wherein B symbolizes a hydrophilic region of the particular crosslinking agent molecule and A in each case symbolizes hydrophobic regions, which can also be of different chemical nature within one molecule.

However, structural diagrams such as

  (4)

  (5)

(6)

  (6)

(7)

  (7)

(8)

  (8)

and analogously formed structures which are yet more complex also fall entirely within the context of the invention submitted here.

Structural diagrams as follows:

  (9)

  (10)

(11)

  (11)

(12)

  (12)

-continued

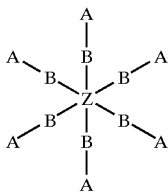
(13)

wherein Z here is a central unit, which can be hydrophilic or hyrophobic and as a rule consists of an oligo- or polyfunctional molecular radical, also fall within the context of the invention submitted here.

Thickeners with a higher degree of branching of course also fall within the context of the present invention.

For example, Z in diagram (10) can consist of a glyceryl radical, the three OH functions of which pass into the regions B, which in their turn can be, for example, polyoxyethylene chains of equal or unequal length, and the terminal OH groups of which are esterified with a longer-chain fatty acid. Partial substitution on the glycercol is also conceivable, as a result of which structures which correspond to diagram (9) can form.

The hydrophilic groups B can advantageously be chosen such that the crosslinking agent overall is water-soluble or at least dispersible in water, in which case the hydrophobic content of the groups A should then be over-compensated.

The following more specific structure diagrams can be followed, for example, for structure diagram (1):

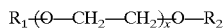

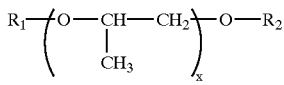

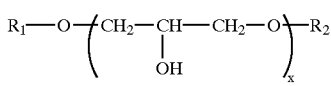

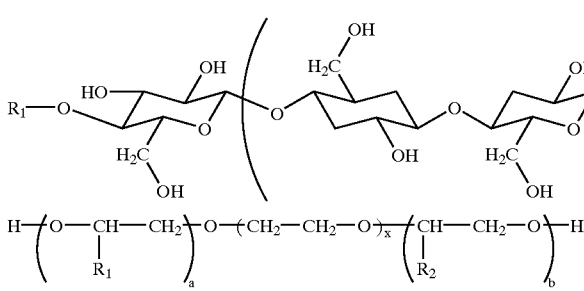

wherein $R^1$, $R_2$, $R_3$, $R_4$, $R_5$ and $R_6$ independently of one another can be branched or unbranched, saturated or unsaturated, cyclic or chain-like aliphatic, aromatic or heteroaromatic radicals, f or example branched or unbranched or cyclic alkyl or alkanoyl radicals, aryl or aroyl radicals which are unsubstituted or substituted by alkyl or aryl substituents, or also alkylated or arylated organylsilyl radicals. x here is numbers which enable the total molecule to be soluble or at least dispersible in water, and is typically chosen from the range greater than 10, advantageously from the range 20–300. a and b are numbers which are chosen, depending on x, such that the total molecule has an at least adequate water-solubility or water-dispersibility. In the individual case, for example if the thickener is chosen from the group consisting of derivatized polysaccharides, x can also assume still considerably higher values than 300, even several millions. This is known per se to the expert and requires no further explanation.

For the structure diagram (2) for example, the following more specific structure diagrams can be followed:

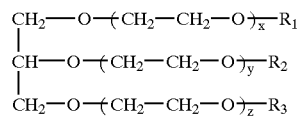

wherein $R_1$, $R_2$, and $R_3$ independently of one another can be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. x, y and z independently of one another here are numbers which enable the total molecule to be soluble or at least dispersible in water, and are typically chosen from the range greater than 10, advantageously from the range 20–300.

Partial substitution is also conceivable here, it being possible for one or more of the indices x, y or z to assume the value zero and for one or more of the radicals $R_1$, $R_2$ or $R_3$ to be hydrogen-atoms.

For structure diagram (3) for example, the following more specific structure diagrams can be followed:

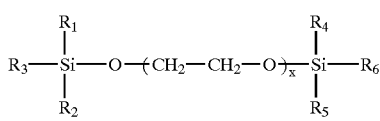

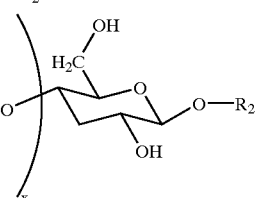

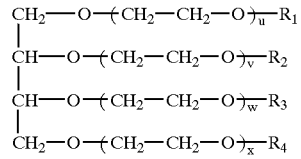

-continued

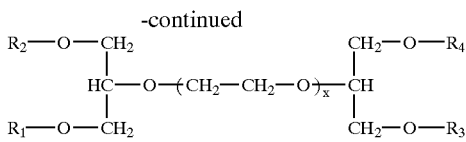

wherein $R_1$, $R_2$, $R_3$ and $R_4$ independently of one another can be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w and x here independently of one another are numbers which enable the total molecule to be soluble or at least dispersible in water, and are typically chosen from the range greater than 10, advantageously from the range 20–300.

It also goes without saying here that partial substitution is conceivable, it being possible for one or more of the indices u, v, w and x to assume the value zero and for one or more of the radicals $R_1$, $R_2$, $R_3$ or $R_4$ to be hydrogen atoms. The substances here of course change into other structure diagrams.

For the structure diagram (9), for example, the following more specific structure diagrams can be followed:

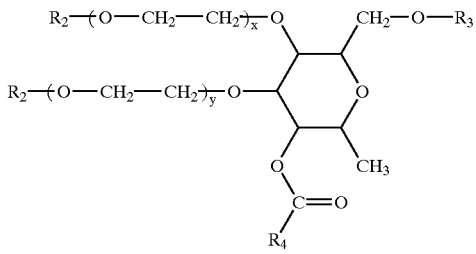

wherein $R_1$, $R_2$, $R_3$ and $R_4$ independently of one another can be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. x and y here independently of one another are numbers which enable the total molecule to be soluble or at least dispersible in water, and are typically chosen from the range greater than 10, advantageously from the range 20–300.

For the structure diagram (10), for example, the following more specific structure diagrams can be followed:

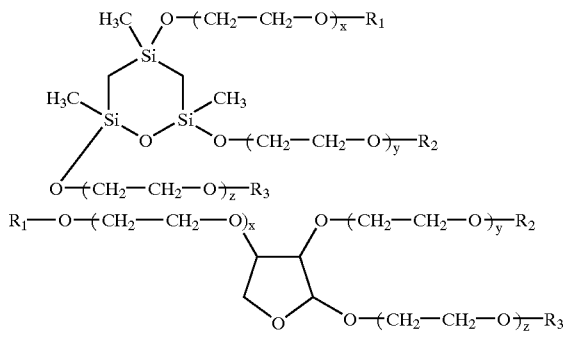

wherein $R_1$, $R_2$ and $R_3$ independently of one another can be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. x, y and z here independently of one another are numbers which enable the total molecule to be soluble or at least dispersible in water, and are typically chosen from the range greater than 10, advantageously from the range 20–300.

For the structure diagram (11) for example, the following more specific structure diagram can be followed:

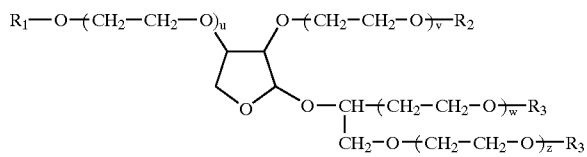

wherein $R_1$, $R_2$, $R_3$ and $R_4$ independently of one another can be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w and x here independently of one another are numbers which enable the total molecule to be soluble or at least dispersible in water, and are typically chosen from the range greater than 10, advantageously from the range 20–300. k, l, m and n here independently of one another can be numbers from 0 to 50.

For the structure diagram (12), for example, the following more specific structure diagram can be followed:

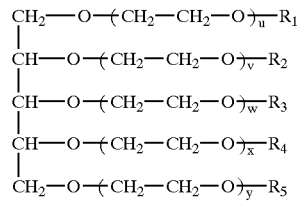

wherein $R_1$, $R_2$, $R_3$, $R_4$ and $R_5$ independently of one another can be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w, x and y here independently of one another are numbers which enable the total molecule to be soluble or at least dispersible in water, and are typically chosen from the range greater than 10, advantageously from the range 20–100.

For the structure diagram (13), for example, the following more specific structure diagram can be followed:

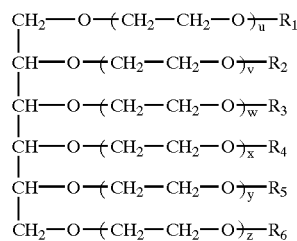

wherein $R_1$, $R_2$, $R_3$, $R_4$, $R_5$ and $R_6$ independently of one another can be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w, x, y and z here independently of one another are numbers which enable the total molecule to be soluble or at least dispersible in water, and are typically chosen from the range greater than 10, advantageously from the range 20–1000.

Where appropriate, it is also advantageous to modify the structure diagrams described above such that renewed branching occurs at the end of the thickener molecule, for example in a manner such as is realized in the group consisting of so-called dendrimers.

Crosslinking agents which have proved to be particularly suitable are those chosen from the group consisting of the polyethylene glycol ethers of the general formula R—O—(—$CH_2$—$CH_2$—O—)$_n$—R', wherein R and R' independently of one another are branched or unbranched alkyl, aryl or alkenyl radicals and n is a number greater than 100, the etherified fatty acid ethoxylates of the general formula R—COO—(—$CH_2$—$CH_2$—O—)$_n$—R', wherein R and R' independently of one another are branched or unbranched alkyl, aryl or alkenyl radicals and n is a number greater than 100, the esterified fatty acid ethoxylates of the general formula R—COO—(—$CH_2$—$CH_2$—O—)$_n$—C(O)—R', wherein R and R' independently of one another are branched or unbranched alkyl, aryl or alkenyl radicals and n is a number greater than 100, the polypropylene glycol ethers of the general formula R—O—(—$CH_2$—CH($CH_3$)—O—)$_n$—R', wherein R and R' independently of one another are branched or unbranched alkyl, aryl or alkenyl radicals and n is a number greater than 100, the esterified fatty acid propoxylates of the general formula R—COO—(—$CH_2$—CH($CH_3$)—O—)$_n$—C(O)—R', wherein R and R' independently of one another are branched or unbranched alkyl, aryl or alkenyl radicals and n is a number greater than 100, the polypropylene glycol ethers of the general formula R—O—$X_n$—$Y_m$—R', wherein R and R' independently of one another are branched or unbranched alkyl, aryl or alkenyl radicals, and wherein X and Y are not identical and are in each case either an oxyethylene group or an oxypropylene group and n and m independently of one another are numbers, the sum of which is greater than 100 and the etherified fatty acid propoxylates of the general formula R—COO—$X_n$—$Y_m$—R', wherein R and R' independently of one another are branched or unbranched alkyl, aryl or alkenyl radicals, and wherein X and Y are not identical and are in each case either an oxyethylene group or an oxypropylene group and n and m independently of one another are numbers, the sum of which is greater than 100.

PEG 150-distearate and PEG 150-dioleate are particularly advantageous. PEG 300-pentaerythrityl tetraisostearate, PEG 120-methylglucose dioleate, PEG 160-sorbitan triisostearate, PEG 450-sorbitol hexaisostearate and PEG 230-glyceryl triisostearate are also advantageously to be used as thickeners.

A slightly modified possibility in the formation of microemulsion gels according to the invention comprises immobilizing the oil droplets by the use of hydrophobically modified, synthetic or naturally occurring polymers. Such polymers are occasionally also called associated thickeners.

Figure 6:
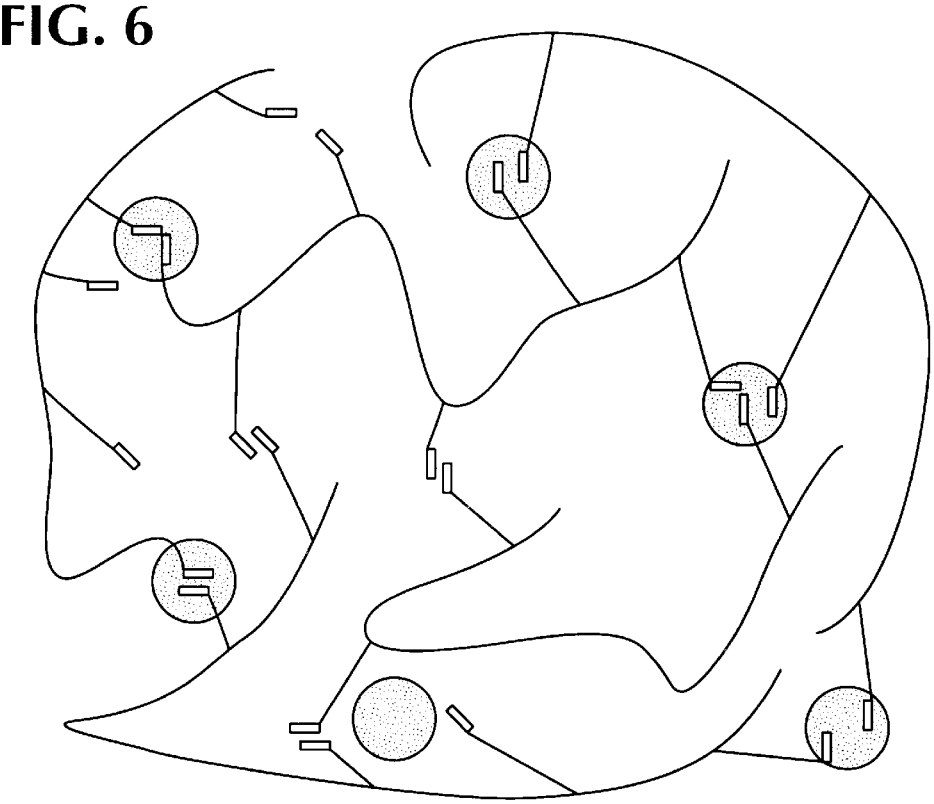
FIG. 6, is a drawing depicting a thickener. The backbone of the thickener which is water soluble or dispersible in water is shown by branched lines. The branching points being hydrophobic groups bonded covalently to the polymer, are symbolized by rectangles.

In FIG. 6, the backbone of a thickener which is water-soluble or dispersible in water is shown by branched lines, the branching points being hydrophobic groups bonded covalently to the polymer, symbolized by rectangles in FIG. 6. The hydrophobic radicals can rest against one another by hydrophobic interaction. Microemulsion droplets can also add onto the crosslinking points by hydrophobic interactions. It is certainly in principle irrelevant in this case whether the hydrophobic radicals are "immersed in" or whether the hydrophobic radicals merely come into contact with the microemulsion droplets on the surface, and stick more or less firmly onto these.

It is accordingly also advantageous, especially if the thickener or thickeners are to be chosen from the group consisting of associated thickeners, to choose hydrophobically substituted polysaccharide derivatives, for example hydrophobically substituted cellulose ethers, hydrophobically substituted starches, alginates, glucans, chitins, dextrans, caseinates, pectins, proteins and gums, and furthermore polyurethanes, polyacrylamides, polyvinyl alcohols, polyacrylates and so on.

The hydrophobically substituted polysaccharide derivatives described in U.S. Pat. No. 5,426,182 are particularly advantageous.

Cetylhydroxyethylcellulose, for example, can be advantageously used.

If appropriate, it may also be advantageous if the thickener or thickeners used according to the invention has or have physiological activity in the context of a cosmetic or pharmaceutical action. Thus, for example, the biosurfactant esters disclosed in German Offenlegungsschrift 43 44 661 can advantageously be used in the context of the present invention.

The formulations according to the invention can advantageously comprise 0.001–20% by weight of one or more thickeners used according to the invention. It is in general preferable to choose the content of thickeners to be less than 10% by weight, in particular less than 5% by weight.

A highly simplified plot of a phase diagram is shown in FIG. 1. The variable parameter P is plotted against the temperature θ as the second variable. P here is a concentration parameter, either the proportion of the oily phase, the proportion of the aqueous phase or the concentration of an emulsifier or of an emulsifier mixture. For systems according to the invention, an O/W emulsion is present at lower temperatures, and the system can pass through the phase inversion range when the temperature is increased. As the temperature is increased further, W/O emulsions are observed. The structure of the system in the phase inversion range is apparently not critical for the present invention. For example, it is conceivable that lamellar phases, bicontinuous phases or cubic, hexagonal or inversely hexagonal phases are present in the phase inversion range, and also that the phase inversion range is composed of several similar or more or less different phases.

The phase inversion range can be represented mathematically as a point quantity within the straight-line coordinate system Σ, which is formed by the parameters of temperature, the concentration of a suitable emulsifier or of an emulsifier mixture in the formulation and the particular concentrations of the oily phase and the aqueous phase, according to:

$$\Sigma = \{O, \theta, m, H, W\}$$

where O—origin of coordinate

θ—temperature m—concentration of the emulsifier/emulsifier mixture

H—concentration of the oily phase

W—concentration of the aqueous phase.

Strictly speaking, the contribution $m_i$ of each individual emulsifier to the total function must of course be taken into account in a multi-component emulsifier system, which, in the case of an i-component emulsifier system, leads to the relationship $$\Sigma = \{O, \theta, m_1, m_2, \ldots, m_i, H, W\}.$$

Figure 2:
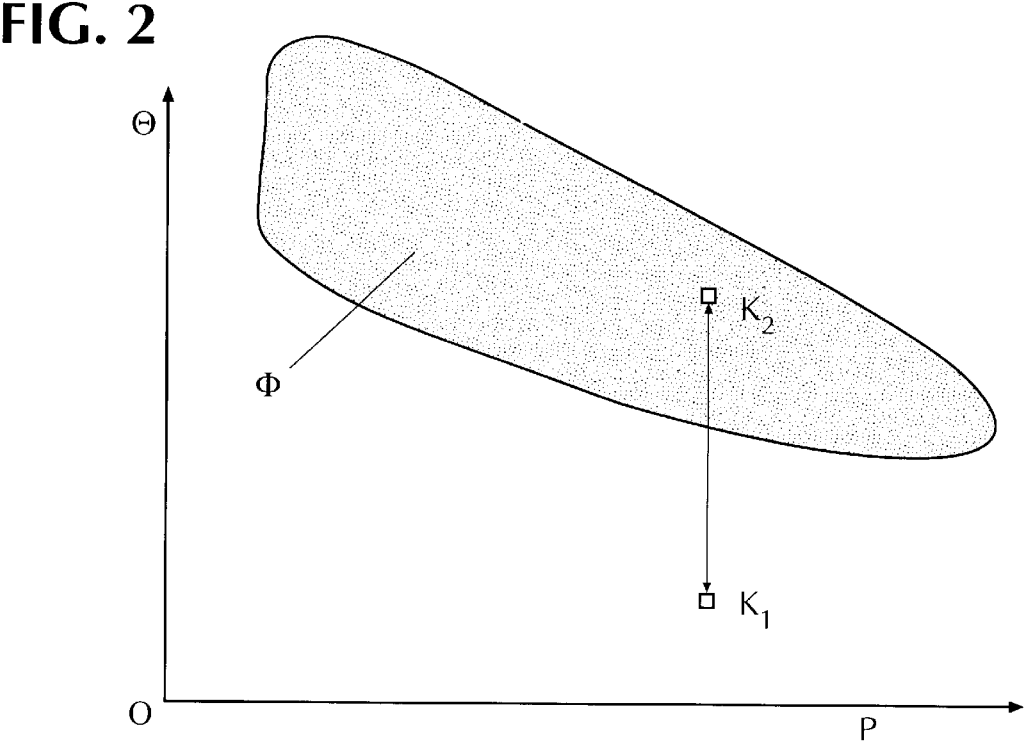
FIG. 2 is a graph depicting phase inversion when passing from a coordinate K1 to a coordinate K2. The variable parameter (P) is plotted against the temperature (Θ).

The phase inversion range $\Phi$ here in the mathematical sense is a continuous region or a large number of continuous regions within the coordinate system $\Sigma$. $\Phi$ represents the total amount of coordinate points $K(\theta, a, m_1, m_2, \ldots, m_i, H, W)$, which determine mixtures according to the invention of an aqueous phase of concentration W, an oily phase of concentration H and i emulsifiers according to the invention of concentration $m_i$ at the temperature $\theta$, and for which, when passing from a coordinate $K_1 \notin \Phi$ to a coordinate $K_2 \in \Phi$, phase inversion occurs, as described in FIG. 2.

It is irrelevant here whether the phase inversion range of a given system is a single continuous (i+3)-dimensional field or comprises several such fields which are continuous but separate from one another, that is to say corresponding to several phase inversion ranges of a given system. In the context of the disclosure submitted herewith, "the" or "a" phase inversion range is therefore always generally referred to, even if two or more such ranges separate from one another are present.

The temperature $\theta$ and the concentration parameter P described above are given as variable coordinates in FIG. 2, where what specific concentration parameter is involved can remain open. On passing from $K_1$ to $K_2$, only the temperature is increased, and the other variables are kept constant.

Under the conditions according to the invention, this process is not reversible, i.e. if the system returns from the coordinate $K_2 \in \Phi$ back to the coordinate $K_1 \notin \Phi$, transparent O/W microemulsions can be obtained which, if thickeners used according to the invention are present or added, render microemulsion gels according to the invention accessible.

The practice of preparing a microemulsion gel according to the invention accordingly advantageously comprises, after choosing suitable raw materials, i.e. the aqueous and oily phases, one or more O/W emulsifiers used according to the invention, the latter present. in concentrations at which phase inversion is possible for the given mixture, one or more thickeners used according to the invention and, if appropriate, further substances, bringing together the individual components, with stirring, bringing about phase inversion by increasing the temperature of the mixture, and thereafter allowing the mixture to cool to room temperature, while continuing to stir, it being possible for the thickener or thickeners used according to the invention to be added at any point in time of the preparation.

Figure 3:
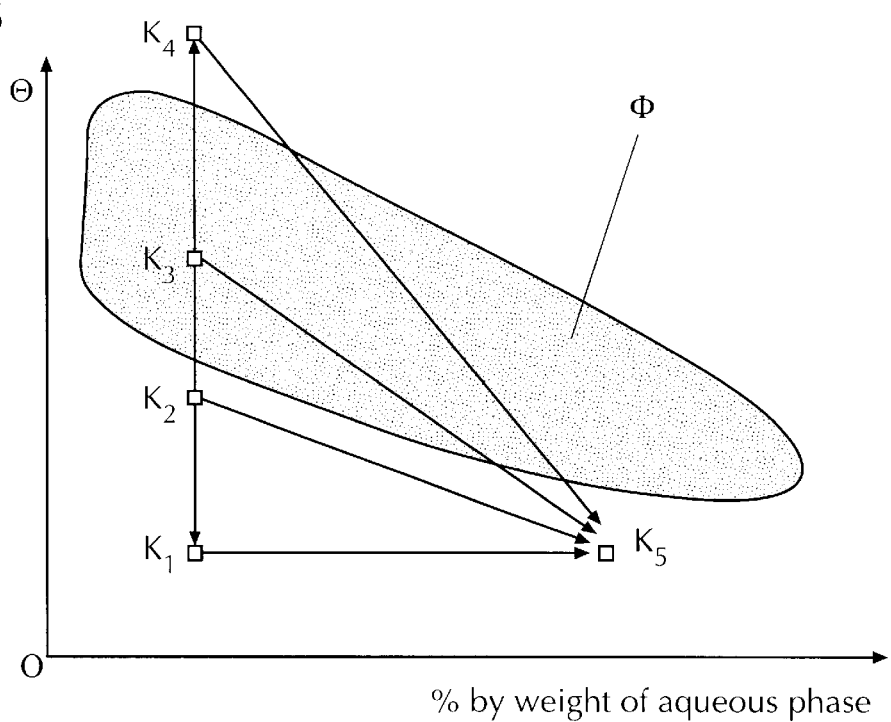
FIG. 3 is a graph wherein the concentration of the aqueous phase is plotted against the temperature.

However, it is also possible to vary several parameters at the same time, as shown in FIG. 3. In FIG. 3, the concentration of the aqueous phase is plotted against the temperature. Starting from the coordinate $K_1 \notin \Phi$ by increasing the temperature while maintaining all other parameters the coordinates $K_2 \notin \Phi$ and $K_4 \notin \Phi$ can be reached, or $K_3 \in \Phi$. Starting from the coordinates $K_3$ and $K_4$, by lowering the temperature back to coordinate $K_1$, while maintaining all other parameters, O/W microemulsions are obtained which, if a thickener used according to the invention is present or added, render microemulsion gels according to the invention accessible.

Starting from the coordinates $K_3$ and $K_4$, by lowering the temperature and by additionally varying the concentration of the oily phase, in FIG. 3 by addition of water, the coordinate $K_5$ can be reached and O/W microemulsions which, if a thickener used according to the invention is present or added, render microemulsion gels according to the invention accessible can be obtained.

In view of FIG. 3, it is logical that starting from the coordinate $K_4$, although this is outside the phase inversion range, systems similar to those which is start from $K_3$ can be obtained, since starting from $K_4$ if the temperature is lowered, the system must certainly also necessarily pass through the phase inversion range.

Furthermore, starting from the coordinate $K_1$, by varying the concentration of the aqueous phase, that is to say, for example, by addition of water, as shown in FIG. 3, the coordinate $K_5$ can be reached and O/W microemulsions which, if a thickener used according to the invention is present or added, render microemulsion gels according to the invention accessible can be obtained. It must first be mentioned, however, that in this case an O/W microemulsion, to a certain extent as a concentrate, must already be present, which is then converted into an O/W microemulsion of different composition by dilution, and this, if a thickener used according to the invention is present or added, renders microemulsion gels according to the invention accessible.

However, after all, it was astonishing and is therefore an independent inventive step that, starting from the coordinate $K_2$, which lies outside the phase inversion range, whether by simply varying the temperature back to the coordinate $K_1$ or by additionally varying the concentration of the oily phase, that is to say, for example, by additional dilution with an aqueous phase to the coordinate $K_5$, O/W microemulsions are also obtainable, which, if a thickener according to the invention is present or added, render microemulsion gels according to the invention accessible, without passing through phase inversion.

This is advantageously effected by bringing a mixture of the base components, comprising the aqueous phase, the oily phase, one or more of the O/W emulsifiers used according to the invention, if desired one or more W/O emulsifiers, one or more thickeners used according to the invention and if desired further auxiliaries, additives and/or active compounds, which form an O/W emulsion below the phase inversion temperature range, to a temperature at which the components which are soluble in the oily phase are present either in dissolved form or at least in the molten state, and which corresponds at least to the melting point of the highest-melting oily component which is not present in the dissolved state, which is below the phase inversion temperature range of the system, thereafter cooling the resulting mixture to room temperature it being possible for the thickener or thickeners used according to the invention to be added at any point in time of the preparation.

This process according to the invention is particularly suitable if heat-sensitive or readily volatile substances are to be incorporated into the O/W microemulsion gels according to the invention. Furthermore, this process, which is to be carried out at relatively low temperatures, is energy-saving compared with customary processes.

Figure 4:
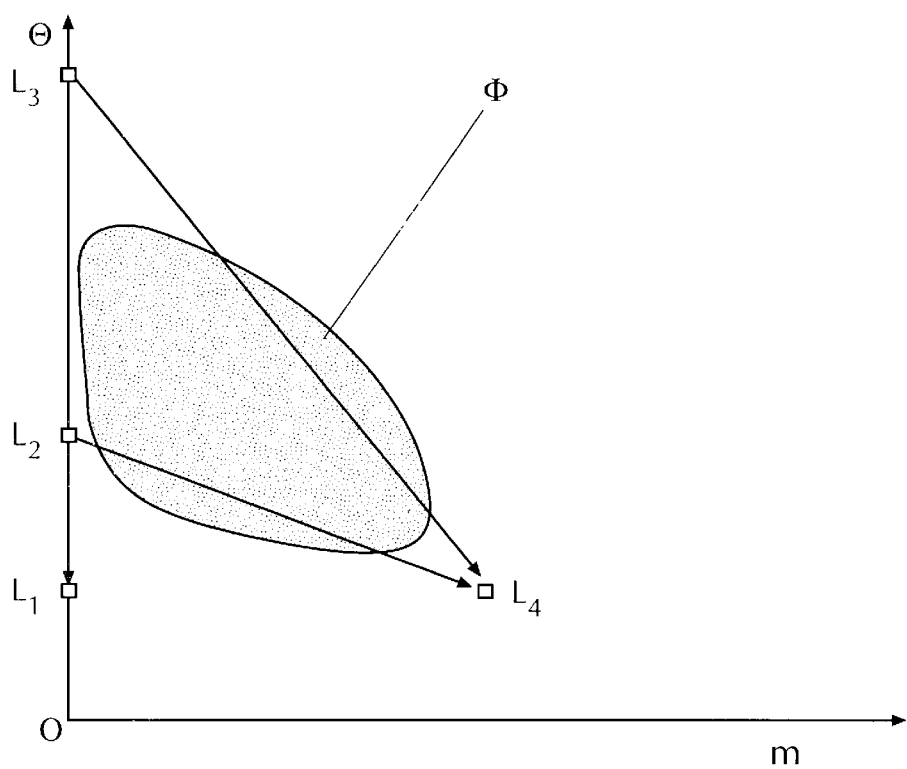
FIG. 4 is a graph depicting the case in which no O/W emulsifier according to the invention is initially present in the coordinate L1, and in which the system is brought to a coordinate L3∉φ or to a coordinate L2∉φ by increasing the temperature.
Figure 5:
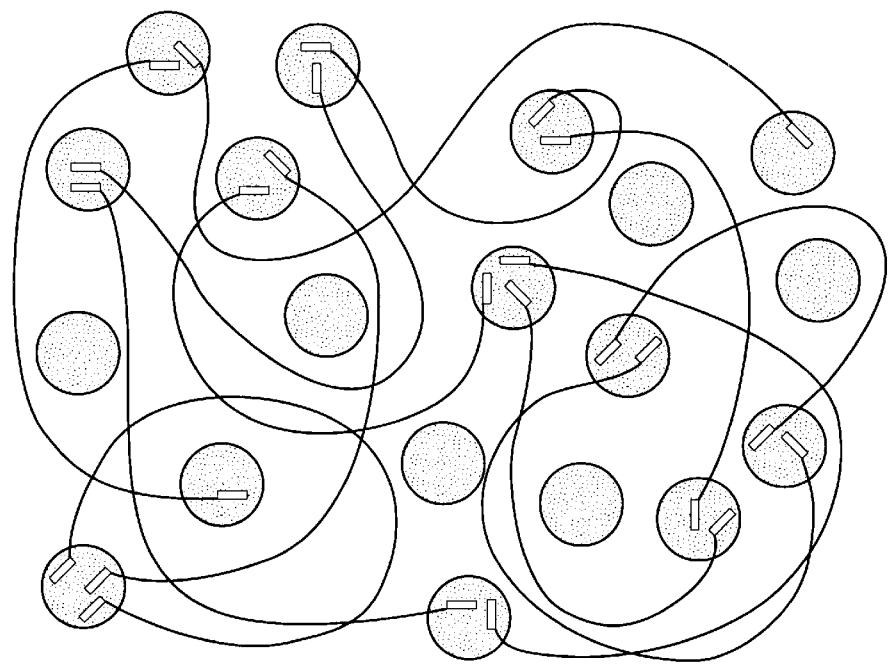
FIG. 5 is a drawing depicting microemulsion droplets of an O/W emulsion, which are shown as shaded circles. The microemulsion droplets are joined to one another by the cross linking agent molecules shown as lines. The hydrophobic radicals are symbolized by rectangles at both ends.

FIG. 4 describes the case in which no O/W emulsifier according to the invention is initially present in the coordinate $L_1$, and in which the system is brought to a coordinate $L_3 \notin \Phi$ or to a coordinate $L_2 \notin \Phi$ by increasing the temperature. The coordinate $L_2$ can of course also be achieved by cooling a system present in the coordinate $L_3$. The coordinates $L_2$ and $L_3$, in which, for example, W/O emulsions can be present, differ in principle only in that the temperature assigned to $L_3$ is higher than that temperature which can be assigned to the phase inversion temperature range.

The presence of an additional W/O emulsifier for systems which are symbolized in FIG. 4 is not absolutely essential, but advantageous. Addition of an OW emulsifier according to the invention or of several such emulsifiers in the coordinate $L_2$ or $L_3$, on lowering the temperature, conveys the system to the coordinate $L_4$, at which an O/W microemulsion which, if a thickener used according to the invention is present or added, renders microemulsion gels according to the invention accessible is then present.

Another advantageous embodiment of the process according to the invention accordingly comprises, after choice of suitable raw materials, i.e. the aqueous and oily phases and, if appropriate, further substances, bringing the individual components, with stirring, to a temperature at which phase inversion is possible for the given mixture and, by adding the O/W emulsifier used according to the invention or the O/W emulsifiers used according to the invention to the mixture, bringing about phase inversion, and thereafter allowing the mixture to cool to room temperature, while continuing to stir, it being possible for the thickener or thickeners used according to the invention to be added at any point in time of the preparation.

It is not beyond the ability of the expert to determine the suitable temperature range within which a given mixture can pass through phase inversion by simple experiments. This temperature range is usually to be chosen between 70 and 95° C., but in an individual case can also be above or below this.

In practice, it is possible and, where appropriate, even advantageous for the temperature range which can be assigned to the phase inversion range also to be exceeded during the preparation of a microemulsion according to the invention, since this range will then necessarily be passed through on cooling to room temperature.

In the context of the present invention, particularly advantageous are microemulsion gels (a) based on microemulsions of the oil-in-water type, which comprise a discontinuous oily phase and a continuous aqueous phase comprising at least one polyethoxylated or polypropoxylated or polyethoxylated and polypropoxylated O/W emulsifier the polyethoxylated or polypropoxylated or polyethoxylated and polypropoxylated O/W emulsifier or the polyethoxylated or polypropoxylated or polyethoxylated and polypropoxylated O/W emulsifiers being chosen from the group consisting of the fatty alcohol ethoxylates of the general formula $R-O-(-CH_2-CH_2-O-)_n-H$, wherein R is a branched or unbranched alkyl, aryl or alkenyl radical and n is a number from 10 to 50, the ethoxylated wool wax alcohols the polyethylene glycol ethers of the general formula $R-O-(-CH_2-CH_2-O-)_n-R'$, wherein R and R' independently of one another are branched or unbranched alkyl or alkenyl radicals and n is a number from 10 to 80, the fatty acid ethoxylates of the general formula $R-COO-(-CH_2-CH_2-O-)_n-H$, wherein R is a branched or unbranched alkyl or alkenyl radical and n is a number from 10 to 40, the etherified fatty acid ethoxylates of the general formula $R-COO-(-CH_2-CH_2-O-)_n-R'$, wherein R and R' independently of one another are branched or unbranched alkyl or alkenyl radicals and n is a number from 10 to 80, the esterified fatty acid ethoxylates of the general formula $R-COO-(-CH_2-CH_2-O-)_n-C(O)-R'$, wherein R and R' independently of one another are branched or unbranched alkyl or alkenyl radicals and n is a number from 10 to 80, the polyethylene glycol glycerol fatty acid esters of saturated and/or unsaturated, branched and/or unbranched fatty acids having a degree of ethoxylation of between 3 and 50, the ethoxylated sorbitan esters having a degree of ethoxylation of 3 to 100 , the cholesterol ethoxylates having a degree of ethoxylation of between 3 and 50, the ethoxylated triglycerides having a degree of ethoxylation of between 3 and 150, the alkyl ether-carboxylic acids of the general formula $R-O-(-CH_2-CH_2-O-)_n-CH_2-COOH$ or cosmetically or pharmaceutically acceptable salts thereof, wherein R is a branched or unbranched alkyl or alkenyl radical having 5–30 C atoms and n is a number from 5 to 30, the polyoxyethylene sorbitol fatty acid esters based on branched or unbranched alkanoic or alkenoic acids and having a degree of ethoxylation of 5 to 100, for example of the sorbeth type, the alkyl ether-sulphates and the acids on which these sulphates are based, of the general formula $R-O-(-CH_2-CH_2-O-)_n-SO_3-H$, with cosmetically or pharmaceutically acceptable cations, wherein R is a branched or unbranched alkyl or alkenyl radical having 5–30 C atoms and n is a number from 1 to 50, the fatty alcohol propoxylates of the general formula $R-O-(-CH_2-CH(CH_3)-O-)_n-H$, wherein R is a branched or unbranched alkyl or alkenyl radical and n is a number from 10 to 80, the polypropylene glycol ethers of the general formula $R-O-(-CH_2-CH(CH_3)-O-)_n-R'$, wherein R and R' independently of one another are branched or unbranched alkyl or alkenyl radicals and n is a number from 10 to 80, the propoxylated wool wax alcohols, the etherified fatty acid propoxylates of the general formula $R-COO-(-CH_2-CH(CH_3)-O-)_n-C(O)-R'$, wherein R and R' independently of one another are branched or unbranched alkyl or alkenyl radicals and n is a number from 10 to 80, the esterified fatty acid propoxylates of the general formula $R-COO-(-CH_2-CH(CH_3)-O-)_n-H$, wherein R and R' independently of one another are branched or unbranched alkyl or alkenyl radicals and n is a number from 10 to 80, the fatty acid propoxylates of the general formula $R-COO-(-CH_2-CH(CH_3)-O-)_n-H$, wherein R is a branched or unbranched alkyl or alkenyl radical and n is a number from 10 to 80, the polypropylene glycol glycerol fatty acid esters of saturated and/or unsaturated, branched and/or unbranched fatty acids having a degree of propoxylation of between 3 and 80, the propoxylated sorbitan esters having a degree of propoxylation of 3 to 100, the cholesterol propoxylates having a degree of propoxylation of 3 to 100, the propoxylated triglycerides having a degree of propoxylation of 3 to 100, the alkyl ether-carboxylic acids of the general formula $R-O-(-CH_2-CH(CH_3)-O-)_n-CH_2-COOH$ and cosmetically or pharmaceutically acceptable salts thereof, wherein R is a branched or unbranched alkyl or alkenyl radical and n is a number from 3 to 50, the alkyl ether-sulphates and the acids on which these sulphates are based, of the general formula R—O—(—CH$_2$—CH(CH$_3$)—O—)$_n$—SO$_3$—H, with cosmetically or pharmaceutically acceptable cations, wherein R is a branched or unbranched alkyl or alkenyl radical having 5–30 C atoms and n is a number from 1 to 50, the fatty alcohol ethoxylates/propoxylates of the general formula R—O—X$_n$—Y$_m$—H, wherein R is a branched or unbranched alkyl or alkenyl radical, and wherein X and Y are not identical and are in each case either an oxyethylene group or an oxypropylene group and n and m independently of one another are numbers from 5 to 50, the polypropylene glycol ethers of the general formula R—O—X$_n$—Y$_m$—R', wherein R and R' independently of one another are branched or unbranched alkyl or alkenyl radicals, and wherein X and Y are not identical and are in each case either an oxyethylene group or an oxypropylene group and n and m independently of one another are numbers from 5 to 100, the etherified fatty acid propoxylates of the general formula R—COO—X$_n$—Y$_m$—R', wherein R and R' independently of one another are branched or unbranched alkyl or alkenyl radicals, and wherein X and Y are not identical and are in each case either an oxyethylene group or an oxypropylene group and n and m independently of one another are numbers from 5 to 100, the fatty acid ethoxylates/propoxylates of the general formula R—COO—X$_n$—Y$_m$—H, wherein R is a branched or unbranched alkyl or alkenyl radical and wherein X and Y are not identical and are in each case either an oxyethylene group or an oxypropylene group and n and m independently of one another are numbers from 5 to 50, if desired comprising one or more W/O emulsifiers, having an emulsifier content of less than 20% by weight, based on the total weight of the emulsion, are obtainable by bringing a mixture of the base components, comprising the aqueous phase, the oily phase, one or more of the O/W emulsifiers according to the invention, if desired, one or more W/O emulsifiers, and if desired further auxiliaries, additives and/or active compounds, to a temperature within or above the phase inversion temperature range, and thereafter cooling it to room temperature, (b) those in which the droplets of the discontinuous oily phase are joined to one another by one or more crosslinking substances, the molecules of which are distinguished by at least one hydrophilic region which has an extension which is capable of bridging the distance between the microemulsion droplets, and by at least one hydrophobic region which is capable of entering into hydrophobic interaction with the microemulsion droplets.

It is particularly advantageous if the polyethoxylated or polypropoxylated or polyethoxylated and polypropoxylated O/W emulsifier or the polyethoxylated or polypropoxylated or polyethoxylated and polypropoxylated O/W emulsifiers is or are. chosen from the group consisting of the fatty alcohol ethoxylates of the general formula R—O—(—CH$_2$—CH$_2$—O—)$_n$—H, wherein R is a branched or unbranched alkyl or alkenyl radical having 5–30 C atoms and n is a number from 10 to 25, the ethoxylated wool wax alcohols having HLB values of 11–16, especially advantageously having HLB values of 14.5–15.5, the polyethylene glycol ethers of the general formula R—O—(—CH$_2$—CH$_{2-O-}$)$_n$—R', wherein R and R' independently of one another are branched or unbranched alkyl or alkenyl radicals having 5–30 C atoms and n is a number from 10 to 25, the fatty acid ethoxylates of the general formula R—COO—(—CH$_2$—CH$_2$—O—)$_n$—H, wherein R is a branched or unbranched alkyl or alkenyl radical having 5–30 C atoms and n is a number from 10 to 25, the etherified fatty acid ethoxylates of the general formula R—COO—(—CH$_2$—CH$_{2-O-}$)$_n$—R', wherein R and R' independently of one another are branched or unbranched alkyl or alkenyl radicals having 5–30 C atoms and n is a number from 10 to 50, the esterified fatty acid ethoxylates of the general formula R—COO—(—CH$_2$—CH$_2$—O—)$_n$—C(O)—R', wherein R and R' independently of one another are branched or unbranched alkyl or alkenyl radicals having 5–30 C atoms and n is a number from 10 to 50, the polyethylene glycol glycerol fatty acid esters of saturated and/or unsaturated, branched and/or unbranched fatty acids having 6 to 26 C atoms and a degree of ethoxylation of between 3 and 40, the ethoxylated sorbitan esters having a degree of ethoxylation of 3 to 30, the cholesterol ethoxylates having HLB values of 11–16, especially advantageously having HLB values of 14.5–15.5, the ethoxylated triglycerides having HLB values of 11–16, especially advantageously having HLB values of 14.5–15.5, the alkyl ether-carboxylic acids of the general formula R—O—(—CH$_2$—CH$_2$—O—)$_n$—CH$_2$—COOH and cosmetically or pharmaceutically acceptable salts thereof, wherein R is a branched or unbranched alkyl or alkenyl radical having 5–30 C atoms and n is a number from 10 to 20, the polyoxyethylene sorbitol fatty acid esters based on branched or unbranched alkanoic or alkenoic acids and having a degree of ethoxylation of 10 to 80, for example of the sorbeth type, the alkyl ether-sulphates and the acids on which these sulphates are based, of the general formula R—O—(—CH$_2$—CH$_2$—O—)$_n$—SO$_3$—H, with cosmetically or pharmaceutically acceptable cations, wherein R is a branched or unbranched alkyl or alkenyl radical having 5–30 C atoms and n is a number from 3 to 30, the fatty alcohol propoxylates of the general formula R—O—(—CH$_2$—CH(CH$_3$)—O—)$_n$—H, wherein R is a branched or unbranched alkyl or alkenyl radical having 5–30 C atoms and n is a number from 10 to 30, the polypropylene glycol ethers of the general formula R—O—(—CH$_2$—CH(CH$_3$)—O—)$_n$—R', wherein R and R' independently of one another are branched or unbranched alkyl or alkenyl radicals having 5–30 C atoms and n is a number from 10 to 40, the propoxylated wool wax alcohols having HLB values of 11–16, especially advantageously having HLB values of 14.5–15.5, the fatty acid propoxylates of the general formula R—COO—(—CH$_2$—CH(CH$_3$)—O—)$_n$—H, wherein R is a branched or unbranched alkyl or alkenyl radical having 5–30 C atoms and n is a number from 10 to 40, the etherified fatty acid propoxylates of the general formula R—COO—(—CH$_2$—CH(CH$_3$)—O—)$_n$—R', wherein R and R' independently of one another are branched or unbranched alkyl or alkenyl radicals having 5–30 C atoms and n is a number from 10 to 30, the esterified fatty acid propoxylates of the general formula R—COO—(—CH$_2$—CH(CH$_3$)—O—)$_n$—C(O)—R', wherein R and R' independently of one another are branched or unbranched alkyl or alkenyl radicals having 5–30 C atoms and n is a number from 10 to 50, the polypropylene glycol glycerol fatty acid esters of saturated and/or unsaturated branched and/or unbranched fatty acids having 6 to 26 C atoms and a degree of propoxylation of between 3 and 50, the propoxylated sorbitan esters having a degree of propoxylation of 3 to 80, the cholesterol propoxylates having HLB values of 11–16, especially advantageously having HLB values of 14.5–15.5, the propoxylated triglycerides having HLB values of 11–16, especially advantageously having HLB values of 14.5–15.5, the alkyl ether-carboxylic acids of the general formula R—O—(—CH$_2$—CH(CH$_3$)—O—)$_n$—CH$_2$—COOH and cosmetically or pharmaceutically acceptable salts thereof, wherein R is a branched or unbranched alkyl or alkenyl radical having 5–30 C atoms and n is a number from 10 to 30, the alkyl ether-sulphates and the acids on which these sulphates are based, of the general formula R—O—(—CH$_2$—CH(CH$_3$)—O—)$_n$—SO$_3$—H, with cosmetically or pharmaceutically acceptable cations, wherein R is a branched or unbranched alkyl or alkenyl radical having 5–30 C atoms and n is a number from 1 to 30.

The polyethoxylated or polypropoxylated or polyethoxylated and polypropoxylated O/W emulsifiers used which are particularly advantageous according to the invention are chosen from the group consisting of substances having HLB values of 11–16, especially advantageously having HLB values of 14.5–15.5, if the O/W emulsifiers contain saturated radicals R and R'. If the O/W emulsifiers contain unsaturated radicals R and/or R', or if isoalkyl derivatives are present, the preferred HLB value of such emulsifiers can also be lower or above this figure.

It is advantageous to choose the fatty alcohol ethoxylates from the group consisting of ethoxylated stearyl alcohols, cetyl alcohols and cetylstearyl alcohols (cetearyl alcohols). The following are particularly preferred:

polyethylene glycol 13-stearyl ether (steareth-13), polyethylene glycol 14-stearyl ether (steareth-14), polyethylene glycol 15-stearyl ether (steareth-15), polyethylene glycol 16-stearyl ether (steareth-16), polyethylene glycol 17-stearyl ether (steareth-17), polyethylene glycol 18-stearyl ether (steareth-18), polyethylene glycol 19-stearyl ether (steareth-19), polyethylene glycol 20-stearyl ether (steareth-20), polyethylene glycol 12-isostearyl ether (isosteareth-12), polyethylene glycol 13-isostearyl ether (isosteareth-13), polyethylene glycol 14-isostearyl ether (isosteareth-14), polyethylene glycol 15-isostearyl ether (isosteareth-15), polyethylene glycol 16-isostearyl ether (isosteareth-16), polyethylene glycol 17-isostearyl ether (isosteareth-17), polyethylene glycol 18-isostearyl ether (isosteareth-18), polyethylene glycol 19-isostearyl ether (isosteareth-19), polyethylene glycol 20-isostearyl ether (isosteareth-20), polyethylene glycol 13-cetyl ether (ceteth-13), polyethylene glycol 14-cetyl ether (ceteth-14), polyethylene glycol 15-cetyl ether (ceteth-15), polyethylene glycol 16-cetyl ether (ceteth-16), polyethylene glycol 17-cetyl ether (ceteth-17), polyethylene glycol 18-cetyl ether (ceteth-18), polyethylene glycol 19-cetyl ether (ceteth-19), polyethylene glycol 20-cetyl ether (ceteth-20), polyethylene glycol 13-isocetyl ether (isoceteth-13), polyethylene glycol 14-isocetyl ether (isoceteth-14), polyethylene glycol 15-isocetyl ether (isoceteth-15), polyethylene glycol 16-isocetyl ether (isoceteth-16), polyethylene glycol 17-isocetyl ether (isoceteth-17), polyethylene glycol 18-isocetyl ether (isoceteth-18), polyethylene glycol 19-isocetyl ether (isoceteth-19), polyethylene glycol 20-isocetyl ether (isoceteth-20), polyethylene glycol 12-oleyl ether (oleth-12), polyethylene glycol 13-oleyl ether (oleth-13), polyethylene glycol 14-oleyl ether (oleth-14), polyethylene glycol 15-oleyl ether (oleth-15), polyethylene glycol 12-lauryl ether (laureth-12), polyethylene glycol 12-isolauryl ether (isolaureth-12), polyethylene glycol 13-cetylstearyl ether (ceteareth-13), polyethylene glycol 14-cetylstearyl ether (ceteareth-14), polyethylene glycol 15-cetylstearyl ether (ceteareth-15), polyethylene glycol 16-cetylstearyl ether (ceteareth-16), polyethylene glycol 17-cetylstearyl ether (ceteareth-17), polyethylene glycol 18-cetylstearyl ether (ceteareth-18), polyethylene glycol 19-cetylstearyl ether (ceteareth-19), polyethylene glycol 20-cetylstearyl ether (ceteareth-20).

It is furthermore advantageous to choose the fatty acid ethoxylates from the following group:

polyethylene glycol 20-stearate, polyethylene glycol 21-stearate, polyethylene glycol 22-stearate, polyethylene glycol 23-stearate, polyethylene glycol 24-stearate, polyethylene glycol 25-stearate, polyethylene glycol 12-isostearate, polyethylene glycol 13-isostearate, polyethylene glycol 14-isostearate, polyethylene glycol 15-isostearate, polyethylene glycol 16-isostearate, polyethylene glycol 17-isostearate, polyethylene glycol 18-isostearate, polyethylene glycol 19-isostearate, polyethylene glycol 20-isostearate, polyethylene glycol 21-isostearate, polyethylene glycol 22-isostearate, polyethylene glycol 23-isostearate, polyethylene glycol 24-isostearate, polyethylene glycol 25-isostearate, polyethylene glycol 12-oleate, polyethylene glycol 13-oleate, polyethylene glycol 14-oleate, polyethylene glycol 15-oleate, polyethylene glycol 16-oleate, polyethylene glycol 17-oleate, polyethylene glycol 18-oleate, polyethylene glycol 19-oleate, polyethylene glycol 20-oleate.

Sodium laureth-11-carboxylate can advantageously be used as an ethoxylated alkyl ether-carboxylic acid or salt thereof.

Sodium laureth-(1-4)-sulphate can advantageously be used as an alkyl ether-sulphate.

Polyethylene glycol 30-cholesteryl ether can advantageously be used as an ethoxylated cholesterol derivative. Polyethylene glycol 25-soyasterol has also proved suitable.

Polyethylene glycol 60-(evening primrose glycerides) can advantageously be used as ethoxylated triglycerides.

It is furthermore advantageous to choose the polyethylene glycol glycerol fatty acid esters from the group consisting of polyethylene glycol 20-glyceryl laurate, polyethylene glycol 21-glyceryl laurate, polyethylene glycol 22-glyceryl laurate, polyethylene glycol 23-glyceryl laurate, polyethylene glycol 6-glyceryl caprate, polyethylene glycol 20-glyceryl oleate, polyethylene 20-glyceryl isostearate polyethylene glycol 18-glyceryl oleate/cocoate.

It is also favourable to choose the sorbitan esters from the group consisting of polyethylene glycol 20-sorbitan monolaurate, polyethylene glycol 20-sorbitan monostearate, polyethylene glycol 20-sorbitan monoisostearate, polyethylene glycol 20-sorbitan monopalmitate and polyethylene glycol 20-sorbitan monooleate.

W/O emulsifiers which can be employed as optional emulsifiers which are nevertheless advantageous according to the invention are: fatty alcohols having 8 to 30 carbon atoms, monoglycerol esters of saturated and/or unsaturated, branched and/or unbranched alkanecarboxylic acids having a chain length of 8 to 24, in particular 12–18 C atoms, diglycerol esters of saturated and/or unsaturated, branched and/or unbranched alkanecarboxylic acids having a chain length of 8 to 24, in particular 12–18 C atoms, monoglycerol ethers of saturated and/or unsaturated, branched and/or unbranched alcohols having a chain length of 8 to 24, in particular 12–18 C atoms, diglycerol ethers of saturated and/or unsaturated, branched and/or unbranched alcohols having a chain length of 8 to 24, in particular 12–18 C atoms, propylene glycol esters of saturated and/or unsaturated, branched and/or unbranched alkanecarboxylic acids having a chain length of 8 to 24, in particular 12–18 C atoms and sorbitan esters of saturated and/or unsaturated, branched and/or unbranched alkanecarboxylic acids having a chain length of 8 to 24, in particular 12–18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, saccharose distearate, cetyl alcohol, stearyl alcohol, arachidyl alcohol, behenyl alcohol, isobehenyl alcohol, selachyl alcohol, chimyl alcohol, polyethylene glycol 2-stearyl ether (steareth-2), glyceryl monolaurate, glyceryl monocaprate and glyceryl monocaprylate.

It is possible according to the invention to keep the total content of emulsifiers at less than 15% by weight, based on the total weight of the microemulsion gels according to the invention. It is preferable to keep the total content of emulsifiers at less than 10% by weight, in particular less than 8% by weight, based on the total weight of the microemulsion gels.

The oily phase of the microemulsion gels according to the invention is advantageously chosen from the group consisting of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, and from the group consisting of esters of aromatic carboxylic acids and saturated and/or unsaturated, branched and/or unbranched alcohols having a chain length of 3 to 30 C atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isoocyl stearate, isononyl stearate, isononyl isononoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and naturally occuring mixtures of such esters, for example jojoba oil.

The oily phase can furthermore advantageously be chosen from the group consisting of branched and unbranched hydrocarbons and waxes, silicon oils, dialkyl ethers and the group consisting of saturated or unsaturated, branched or unbranched alcohols, as well as fatty acid triglycerides, that is to say the triglycerol esters of saturated and/or unsaturated, branched and/or unbranched alkanecarboxylic acids having a chain length of 8 to 24, in particular 12–18 C atoms. The fatty acid triglycerides can advantageously be chosen, for example, from the group consisting of synthetic, semi-synthetic and naturally occurring oils, for example olive oil, sunflower oil, soya oil, groundnut oil, rape oil, almond oil, palm oil, coconut oil, palm kernel oil and so on.

Any desired mixtures of such oil and wax components can also advantageously be employed in the context of the present invention.

If appropriate, it may also be advantageous to employ waxes, for example cetyl palmitate, as the sole lipid component of the oily phase. In such cases, the O/W microemulsions according to the invention can also be obtained, where appropriate, as microdispersions of solid wax particles.

The oily phase is advangaeously chosen from the group consisting of 2-ethylhexyl isostearate, octyldodecanol, isotridecyl isononanoate, isoeicosan, 2-ethylhexyl cocoate, $C_{12-15}$-alkyl benzoate, capryl/capric acid triglyceride and dicaprylyl ether.

Mixtures of $C_{12-15}$-alkyl benzoate and 2-ethylhexyl isostearate, mixtures of $C_{12-14}$-alkyl benzoate and isotridecyl isononanoate and mixtures of $C_{12-15}$-alkyl benzoate, 2-ethylhexyl isostearate and isotridecyl isononanoate are particularly advantageous.

Of the hydrocarbons, paraffin oil, squalane and squalene are advantageously to be used in the context of the present invention.

The oily phase can furthermore advantageously have a content of cyclic or linear silicone oils or consist completely of such oils, but it is preferable to use an additional content of other oily phase components, in addition to the silicone oil or the silicone oils.

Cyclomethicone (octamethylcyclotetrasiloxane) is advantageously employed as a silicone oil to be used according to the invention. However, other silicone oils can also advantageously be used in the context of the present invention, for example hexamethylcyclotrisiloxane, polydimethylsiloxane and poly(methylphenylsiloxane).

An embodiment of the present invention which is also regarded as advantageous is a process for the preparation of O/W microemulsion gels which comprise:

(1) an aqueous phase, if desired comprising customary substances which are soluble or dispersible in water, (2) an oily phase which is composed essentially of constituents of low volatility and which, if desired, comprises customary substances which are soluble or dispersible in the oily phase, (3) one or more polyethoxylated O/W emulsifiers and/or one or more polypropoxylated O/W emulsifiers and/or one or more polyethoxylated and polypropoxylated O/W emulsifiers, (4) if desired, one or more W/O emulsifiers, (5) a thickener according to the invention, characterized in that (a) the initial concentrations of the oily phase, the aqueous phase and, if desired, one or more W/O emulsifiers are chosen and these constituents are added to one another, (b) the initial concentration of the OW emulsifier or emulsifiers, which can also be zero, if appropriate, is chosen and this or these OW emulsifier or emulsifiers are added to the mixture obtained in (a), (c) the mixture obtained in (b) having a starting temperature, (d) the mixture obtained in (b), by suitable variation of at least one parameter chosen from the group consisting of temperature and the concentration or concentrations of at least one of the emulsifiers chosen and/or of the oily phase and/or of the aqueous phase, passes through the phase inversion range between W/O emulsions and O/W emulsions and is brought into the range where the mixture is present as an O/W emulsion or O/W microemulsion, (e) the mixture obtained in (d) is then subjected to further processing steps, if appropriate, (f) it being possible for the thickener or thickeners used according to the invention to be added at any point in time of the preparation.

Processes which are equally advantageous according to the invention are those in which the variation in the parameter or parameters comprises (d1) varying the temperature of the mixture, at a given concentration of the O/W emulsifier or of the plurality of O/W emulsifiers and of the aqueous phase and of the oily phase, or (d2) varying the concentration of at least one O/W emulsifier at a given temperature, or (d3) varying the concentration of the oily phase and/or the concentration of the aqueous phase at a given temperature and a given concentration of at least one O/W emulsifier.

Where appropriate, it may be preferred, according to the invention, to vary several parameters simultaneously or in succession.

The microemulsion gels according to the invention are advantageously prepared by bringing a mixture of the base components, comprising the aqueous phase, the oily phase, one or more of the O/W emulsifiers according to the invention, if desired one or more W/O emulsifiers, and if desired further auxiliaries, additives and/or active compounds, which form an O/W emulsion below the phase inversion temperature range, to a temperature which corresponds at least to the melting point of the highest-melting oil component, but if appropriate is below the phase inversion temperature range of the system, and thereafter cooling the microemulsion formed to room temperature, it being possible for the thickener or thickeners used according to the invention to be added at any point in time of the preparation. The entire operation is preferably carried out with stirring.

The microemulsions according to the invention are also advantageously prepared by bringing a mixture of the base components, comprising the aqueous phase, the oily phase, one or more of the O/W emulsifiers according to the invention, if desired one or more W/O emulsifiers, and if desired further auxiliaries, additives and/or active compounds, which form an O/W emulsion below the phase inversion temperature range, to a temperature above or within the phase inversion temperature range and thereafter cooling the microemulsion formed to room temperature, it being possible for the thickener or thickeners used according to the invention to be added at any point in time of the preparation. The entire operation is preferably carried out with stirring.

According to the invention, advantageous O/W microemulsion gels can be obtained, the proportion of the O/W emulsifier is less than 20% by weight, in particular less than 15% by weight, based on the total weight of the formulation, and less than 5% by weight of an additional W/O emulsifier is present, it being possible for the thickener or thickeners used according to the invention to be added at any point in time of the preparation.

In the individual case, it is possible here that the concentrations are slightly above or below the abovementioned limits, and nevertheless the emulsion types in question are obtained. In view of the widely scattered diversity of suitable emulsifiers and oil constituents, this is not unexpected to the expert, so that he knows that falling above or below such limits does not depart from the basis of the present invention.

The microemulsion gels according to the invention advantageously comprise electrolytes, in particular one or more salts with the following anions: chlorides, and furthermore inorganic oxo-element anions, and of these in particular sulphates, carbonates, phosphates, borates and aluminates. Electrolytes based on organic anions can also advantageously be used, for example lactates, acetates, benzoates, propionates, tartrates, citrates and many others. Comparable effects can also be achieved by ethylenediaminetetraacetic acid and salts thereof.

Cations of the salts which are preferably used are ammonium, alkylammonium, alkali metal, alkaline earth metal, magnesium, iron and zinc ions. It does not need mentioning that in cosmetics, only physiologically acceptable electrolytes should be used. Special medical uses of the microemulsions according to the invention, on the other hand, can at least in principle necessitate the use of electrolytes which should not be used without medical supervision.

Potassium chloride, sodium chloride, magnesium sulphate, zinc sulphate and mixtures thereof are particularly preferred. Salt mixtures such as occur in natural salt from the Dead Sea are also advantageous.

The concentration of the electrolyte or electrolytes should be about 0.1–10.0 by weight, particularly advantageously about 0.3–8.0% by weight, based on the total weight of the formulation.

The microemulsion gels according to the invention furthermore outstandingly help to smooth the skin, especially if they are provided with one or more substances which promote smoothing of the skin.

If the microemulsion gels according to the invention are bases for cosmetic deodorants/antiperspirants, all the customary active compounds can advantageously be used, for example odour maskers, such as the customary perfume constituents, odour absorbers, for example the laminar silicates described in the Laid-Open Specification DE-P 40 09 347, and of these in particular montmorillonite, kaolinite, ilite, beidellite, nontronite, saponite, hectorite, bentonite and smectite, and furthermore, for example, zinc salts of ricinoleic acid. Germ-inhibiting agents are also capable of being incorporated into the microemulsions according to the invention. Advantageous substances are, for example, 2,4,4'-trichloro-2'-hydroxydiphenyl ether (Irgasan), 1,6-di-(4-chlorophenylbiguanido)hexane (chlorhexidine), 3,4,4'-trichlorocarbanilide, quaternary ammonium compounds, oil of cloves, mint oil, oil of thyme, triethyl citrate, farnesol (3,7,11-trimethyl-2,6,10-dodecatrien-1-ol) and the active agents described in the Patent Laid-Open Specifications DE-37 40 186, DE-39 38 140, DE-42 04 321, DE-42 29 707, DE-42 29 737, DE-42 37 081, DE-43 09 372 and DE-43 24 219.

The customary antiperspirant active compounds can also advantageously be used in the microemulsion gels according to the invention, in particular astringents, for example basic aluminium chlorides.

The cosmetic deodorants according to the invention can be in the form of aerosols, that is to say preparations which can be sprayed from aerosol containers, squeeze bottles or by a pump device, or in the form of liquid compositions which can be applied by means of roll-on devices, but also in the form of microemulsion gels which can be applied from normal bottles and containers.

Suitable propellants for cosmetic deodorants according to the invention which can be sprayed from aerosol containers are the customary known readily volatile liquefied propellants, for example hydrocarbons (propane, butane or isobutane), which can be employed by themselves or as a mixture with one another. Compressed air can also advantageously be used.

The expert of course knows that there are propellant gases which are non-toxic per se and would be suitable in principle for the present invention, but which should nevertheless be omitted because of an unacceptable action on the environment or other concomitant circumstances, in particular chlorofluorohydrocarbons (CFCs).

It has furthermore been found, surprisingly, that if propellants which are soluble in the oily phase, that is to say, for example, customary propane/butane mixtures, are used, the O/W microemulsion gels according to the invention are not only sprayed as aerosol droplets, but develop into fine-bubbled, rich foams as soon as such systems loaded with such propellants experience a release of pressure.

Such after-foaming formulations are therefore also to be regarded as advantageous embodiments of the present invention with an independent inventive step.

If propellants which are insoluble in the oily phase are used, the O/W microemulsion gels according to the invention are sprayed as aerosol droplets.

Those cosmetic and dermatological formulations which are in the form of a sunscreen composition are also favourable. These advantageously additionally comprise, in addition to the active compound combinations according to the invention, at least one UVA filter substance and/or at least one UVB filter substance and/or at least one inorganic pigment.

However, it is also advantageous in the context of the present invention to provide those cosmetic and dermatological formulations of which the main purpose is not protection from sunlight but which nevertheless comprise a content of UV protection substances. Thus, for example, UV-A or UV-B filter substances are usually incorporated into day creams.

Formulations according to the invention can advantageously comprise substances which absorb UV radiation in the UVB range, the total amount of the filter substances being, for example, 0.1% by weight to 30% by weight, preferably 0.5 to 10% by weight, in particular 1 to 6% by weight, based on the total weight of the formulations.

The UVB filters can be oil-soluble or water-soluble. Examples of oil-soluble substances which may be mentioned are, for example:

3-benzylidenecamphor and derivatives thereof, for example 3-(4-methylbenzylidene)camphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate; and 2,4,6-trianilino-(p-carbo-2'-ethyl-1'-hexyloxy)-1,3,5-triazine.

Advantageous water-soluble substances are:

2-phenylbenzimidazole-5-sulphonic acid and salts thereof, for example sodium, potassium or triethanolammonium salts, sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)benzenesulphonic acid and their salts.

The list of UVB filters mentioned, which can be used according to the invention, is of course not intended to be limiting.

The invention also relates to the combination of a UVA filter according to the invention with a UVB filter, and a cosmetic or dermatological formulation according to the invention which also comprises a UVB filter.

It may also be advantageous to employ UVA filters which are usually contained in cosmetic and/or dermatological formulations in formulations according to the invention. Such substances are preferably derivatives of dibenzoylmethane, in particular 1-(4'-tert-butylphenyl)-3-(4'-methoxyphenyl)propane-1,3-dioneandl-phenyl-3-(4'-isopropylphenyl)propane-1,3-dione. The invention also relates to formulations which comprise these combinations. The same amounts of UVA filter substances as have been mentioned for UVB filter substances can be used.

Cosmetic and/or dermatological formulations according to the invention can also comprise inorganic pigments which are usually used in cosmetics for protecting the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide. The amounts mentioned for the above combinations can be used.

An astonishing property of the present invention is that formulations according to the invention are very good vehicles for cosmetic or dermatological active compounds in the skin, advantageous active compounds being antioxidants which can protect the skin from oxidative stress.

According to the invention, the formulations advantageously comprise one or more antioxidants. Favourable antioxidants, which are nevertheless to be used optionally, are all the antioxidants which are suitable or customary for cosmetic and/or dermatological applications. It is advantageous here to use antioxidants as the sole class of active compound, for example if a cosmetic or dermatological use such as combating oxidative stress of the skin is a priority. However, it is also favourable to provide the microemulsion gels according to the invention with a content of one or more antioxidants if the formulations are to serve another purpose, for example as deodorants or sunscreen compositions.

The antioxidants are particularly advantageously chosen from the group consisting of amino acids (for example histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gammalinoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to µmol/kg), and furthermore (metal) chelators (for example α-hydroxy-fatty acids, α-hydroxy-palmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example gamma-linolenic acid, linoleic acid and oleic acid), folic acid and derivatives thereof, ubiquinone and ubiquinol and derivatives thereof, vitamin C and derivatives (for example ascorbyl palmitates, Mg ascorbyl phosphates and ascorbyl acetates), tocopherols and derivatives (for example vitamin E acetate), vitamin A and derivatives (vitamine A palmitate) and coniferyl benzoate of benzoin resin, rutic acid and derivatives thereof, ferulic acid and derivatives thereof, butylhydroxytoluene, butylhydroxyanisole, nordihydroguaiac resin acid, nordihydroguaiaretic acid, trihydroxybutyrophenone, uric acid and derivatives thereof, zinc and derivatives thereof (for example ZnO and $ZnSO_4$), selenium and derivatives thereof (for example seleniummethionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

Oil-soluble antioxidants can particularly advantageously be employed in the context of the present invention.

The amount of antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10k by weight, based on the total weight of the formulation.

It is of course known to the expert that high-quality cosmetic formulations are usually inconceivable without the customary auxiliaries and additives. These include, for example, agents which impart consistency, fillers, perfume, dyestuffs, emulsifiers, additional active compounds, such as vitamins or proteins, light protection agents, stabilizers, insect repellants, alcohol, water, salts and substances having an antimicrobial, proteolytic or keratolytic action.

According to the invention, the active compounds can also very advantageously be chosen from the group consisting of lipophilic active compounds, in particular from the following group:

acetylsalicylic acid, atropine, azulene, hydrocortisone and derivatives thereof, for example hydrocortisone 17-valerate, vitamins, for example ascorbic acid and derivatives thereof, vitamins of the B and D series, very favourably vitamin $B_1$, vitamin $B_{12}$ and vitamin $D_1$, but also bisabolol, unsaturated fatty acids, that is to say the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of plant and animal origin, for example oil of evening primrose, borret oil or current kernel oil, fish oils and cod-liver oil, and also ceramides and ceramide-like compounds and so on.

Although the use of hydrophilic active compounds is of course also favoured according to the invention, it is another advantage of the microemulsion gels according to the invention that the high number of very finely divided droplets renders precisely oil-soluble or lipophilic active compounds biologically available with a particularly high activity.

It is also advantageous to choose the active compounds from the group of re-oiling substances, for example Purcellin oil, Eucerit® and Neocerit®.

It is also possible, and may be advantageous, to add wash-active surfactants to the formulations according to the invention. Aqueous cosmetic cleansing agents according to the invention or low-water or anhydrous cleansing agent concentrates intended for aqueous cleansing can comprise cationic, anionic, nonionic and/or amphoteric surfactants, for example conventional soaps, for example fatty acid salts of sodium, alkyl sulphates, alkyl ether sulphates, alkane- and alkylbenzenesulphonates, sulphoacetates, sulphobetaines, sarcosinates, amidosulphobetaines, sulphosuccinates, sulphosuccinic acid half-esters, alkyl ether-carboxylates, protein-fatty acid condensates, alkylbetaines and aminobetaines, fatty acid alkanolamides and polyglycol ether derivatives.

Cosmetic formulations which are cosmetic cleansing formulations for the skin can be present in liquid or solid form. They preferably comprise at least one anionic, nonionic or amphoteric surface-active substance or mixtures thereof, at least one electrolyte according to the invention and auxiliaries such as are usually used for this purpose. The surface-active substance can preferably be present in the cleansing formulations in a concentration of between 1 and 50% by weight, based on the total weight of the formulations.

Cosmetic formulations which are a shampooing agent preferably comprise at least one anionic, nonionic or amphoteric surface-active substance or mixtures thereof, if appropriate electrolytes and auxiliaries such as are usually used for this purpose. The surface-active substance can preferably be present in the cleansing formulations in a concentration of between 1 and 50% by weight, based on the total weight of the formulations. Cetyltrimethylammonium salts, for example, are advantageously to be used.

The compositions according to the invention intended for cleansing the hair or the skin comprise, in addition to the abovementioned surfactants, water and, if appropriate, the additives customary in cosmetics, for example perfume, thickeners, dyestuffs, deodorants, antimicrobial substances, re-oiling agents, complexing and sequestering agents, pearlescent agents, plant extracts, vitamins, active compounds and the like.

In spite of their oil content, the formulations according to the invention astonishingly have a very good foam development and high cleansing power, and have a highly regenerating action in respect of the general state of the skin. In particular, the formulations according to the invention have the effect of smoothing the skin, reduce the dryness sensation of the skin and make the skin supple.

If the microemulsion gels according to the invention are to be employed for hair care, they can comprise the customary constituents, usually, for example, film-forming polymers. Suitable such polymers having at least partly quaternized nitrogen groups (called "film-forming agents" below) are preferably those which are chosen from the group consisting of substances which, according to INCI nomenclature (International Nomenclature of Cosmetic Ingredients) carry the name "polyquaternium", for example:

Polyquaternium-2 (Chemical Abstracts No. 63451-27-4, for example Mirapol® A-15)

Polyquaternium-5 (Copolymer of acrylamide and β-methacryloxyethyltrimethylammonium methosulphate, CAS No. 26006-22-4)

Polyquaternium-6 (Homopolymer of N,N-dimethyl-N-2-propenyl-2-propene-1-aminium chloride, CAS No. 26062-79-3, for example Merquat® 100

Polyquaternium-7 N,N-Dimethyl-N-2-propenyl-2-propene-1-aminium chloride, polymer with 2-propenamide, CAS No. 26590-05-6, for example Merquat® S Polyquaternium-10 Quaternary ammonium salt of hydroxyethylcellulose, CAS No. 53568-66-4, 55353-19-0, 54351-50-7, 68610-92-4, 81859-24-7, for example Celquat® SC-230M Polyquaternium-11 Vinylpyrrolidone/dimethylaminoethyl methacrylate copolymer/diethyl sulphate reaction product, CAS No. 53633-54-8, for example Gafquat 755N Polyquaternium-16 Vinylpyrrolidone/vinylimidazolinium methochloride copolymer, CAS No. 29297-55-0, for example Luviquat® HM 552

Polyquaternium-17 CAS No. 90624-75-2, for example Mirapol® AD-1

Polyquaternium-19 Quaternized water-soluble polyvinyl alcohol

Polyquaternium-20 Water-dispersible quaternized polyvinyl octadecyl ether

Polyquaternium-21 Polysiloxane-polydimethyldimethylammonium acetate copolymer, for example Abil® B 9905

Polyquaternium-22 Dimethyldiallylammonium chloride/acrylic acid copolymer, CAS No. 53694-7-0, for example Merquat®280

Polyquaternium-24 Polymeric quaternium ammonium salt of hydroxyethylcellulose, reaction product with an epoxide substituted by lauryl dimethylammonium, CAS No. 107987-23-5, for example Quatrisoft® LM-200

Polyquaternium-28 Vinylpyrrolidone/methacrylamidopropyltrimethylammonium chloride copolymer, for example Gafquat® HS-100

Polyquaternium-29 For example Lexquat® CH

Polyquaternium-31 CAS No. 136505-02-7, for example Hypan® QT 100

Polyquaternium-32 N,N,N-Trimethyl-2-[(2-methyl-1-oxo-2-propenyl)oxy]ethanaminium chloride, polymer with 2-propeneamide, CAS No. 35429-19-7

Polyquaternium-37 CAS No. 26161-33-1

Formulations according to the invention for hair care advantageously comprise 0.2–50% by weight of one or more film-forming agents, preferably 5–30% by weight, in particular 10–25% by weight, in each case based on the total weight of the formulations. Such embodiments of the formulations according to the invention care for hair damaged or worn out by environmental influences, or protect against such environmental influences. The formulations according to the invention furthermore impart to the hairstyle a loose fullness and firmness, without having a tacky effect.

Where appropriate, it is possible and advantageous to use the formulations according to the invention as a base for pharmaceutical formulations. Mutatis mutandis, appropriate requirements apply to the formulation of medical formulations. The transitions between pure cosmetics and pure pharmaceuticals are continuous here. All active compound classes are in principle suitable according to the invention as pharmaceutical active compounds, liphophilic active compounds being preferred. Examples are: antihistamines, antiphlogistics, antibiotics, antimycotics, active compounds which promote circulation, keratolytics, hormones, steroids, vitamins and the like.

The cosmetic and dermatological formulations according to the invention can comprise cosmetic auxiliaries such as are usually used in such formulations, for example preservatives, bactericides, virucides, perfumes, substances for preventing foaming, dyestuffs, pigments which have a colouring action, other thickening agents which do not fall under the definition of the thickeners according to the invention, surface-active substances, emulsifiers, softening, humidifying and/or humectant substances, antiinflammatory substances, medicaments, fats, oils, waxes or other customary constituents of a cosmetic or dermatological formulation, such as alcohols, polyols, polymers, foam stabilizers, electrolytes and organic solvents.

Mixtures of the abovementioned solvents are particularly advantageously used.

Other constituents which can be used are fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids, alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

The following examples are intended to illustrate the present invention.

EXAMPLE 1

| Deodorizing formulation | |
|---|---|
| | % by weight |
| Glyceryl isostearate | 2.400 |
| PEG 15-cetylisostearyl alcohol | 4.800 |
| Isotridecyl isononanoate | 1.670 |
| PEG 300 pentaerythrityl tetraisostearate | 1.000 |
| Cyclomethicone | 3.300 |
| Butylene glycol | 3.000 |
| Farnesol | 0.300 |
| Glycerol monocaprate | 0.100 |
| Hydrated aluminium chloride | 4.000 |
| Perfume, antioxidants | q.s |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 2

| Deodorizing formulation | |
|---|---|
| | % by weight |
| Glyceryl isostearate | 1.800 |
| PEG 15-cetylstearyl alcohol | 5.200 |
| Sorbitol | 2.900 |
| Isotridecyl isononanoate | 3.300 |
| PEG 300 pentaerythrityl tetraisostearate | 1.000 |
| Cyclomethicone | 6.600 |
| Glycerol monocaprate | 0.100 |
| Hydrated aluminium chloride | 3.883 |
| Perfume, antioxidants | q.s |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 3

| Deodorizing formulation | |
|---|---|
| | % by weight |
| Glyceryl isostearate | 1.800 |
| PEG 17-cetylstearyl alcohol | 5.200 |
| PEG 300 pentaerythrityl tetraisostearate | 1.000 |
| Isotridecyl isononanoate | 10.000 |
| Sorbitol | 2.900 |
| Glycerol monocaprate | 0.100 |
| Hydrated aluminium chloride | 3.900 |
| Perfume, antioxidants | q.s |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 4

| Deodorizing formulation | |
|---|---|
| | % by weight |
| Sorbitan monoisostearate | 2.300 |
| PEG 15-cetylstearyl alcohol | 4.600 |
| Sorbitol | 2.900 |
| Cyclomethicone | 6.600 |
| PEG 300-pentaerythrityl tetraisostearate | 1.000 |
| Isotridecyl isononanoate | 3.300 |
| Glycerol monocaprate | 0.100 |
| Hydrated aluminium chloride | 3.900 |
| Perfume, antioxidants | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 5

| Deodorizing formulation | |
|---|---|
| | % by weight |
| Diglyceryl monisostearate | 1.800 |
| PEG 15-cetylstearyl alcohol | 5.100 |
| $C_{12-15}$-alkyl benzoate | 5.000 |
| PEG 300-pentaerythrityl tetraisostearate | 1.000 |
| Octyl isostearate | 5.000 |
| Sorbitol | 2.900 |
| Glycerol monocaprate | 0.100 |
| Hydrated aluminum chloride | 3.900 |
| Perfume, antioxidants | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 6

| Deodorizing formulation | |
|---|---|
| | % by weight |
| Diglyceryl monoisostearate | 2.300 |
| PEG 15-cetylstearyl alcohol | 4.600 |
| Cyclomethicone | 6.600 |
| PEG 300-pentaerythrityl tetraisostearate | 1.000 |
| Sorbitol | 2.900 |
| Isotridecylisononanoate | 3.300 |
| Glycerol monocaprate | 0.100 |
| Hydrated aluminium chloride | 3.900 |
| Perfume, antioxidants | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 7

| Deodorizing formulation | |
|---|---|
| | % by weight |
| Glyceryl isostearate | 1.800 |
| PEG 16-stearyl alcohol | 5.100 |
| Octyl isostearate | 3.300 |
| PEG 300-pentaerythrityl tetraisostearate | 1.000 |
| Cyclomethicone | 6.600 |
| Sorbitol | 2.900 |
| Glycerol monocaprate | 0.100 |
| Hydrated aluminium chloride | 3.900 |
| Perfume, antioxidants | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 8

| Deodorizing formulation | |
|---|---|
| | % by weight |
| Propylene glycol monoisostearate | 2.300 |
| PEG 16-cetylstearyl alcohol | 4.600 |
| Isotridecyl isononanoate | 3.300 |
| PEG 300-pentaerythrityl tetraisostearate | 1.000 |
| Cyclomethicone | 6.600 |
| Sorbitol | 2.900 |
| Glycerol monocaprate | 0.100 |
| Hydrated aluminium chloride | 3.900 |
| Perfume, antioxidants | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 9

| Light protection formulation | |
|---|---|
| | % by weight |
| Glyceryl isostearate | 2.400 |
| Isoceteth-20 | 4.800 |
| Cetearylisononanoate | 1.670 |
| PEG 300-pentaerythrityl tetraisostearate | 1.000 |
| Eusolex ® 232 | 3.000 |
| Cyclomethicone | 3.330 |
| NaOH | 0.990 |
| Glycerol | 3.000 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 10

| Skin-care gel | |
|---|---|
| | % by weight |
| Glyceryl isostearate | 2.400 |
| PEG 60-evening primrose glycerides | 4.800 |
| Cetylhydroxyethylcellulose | 4.000 |
| Isotridecyl isononanoate | 3.340 |
| Cyclomethicone | 6.660 |
| Butylene glycol | 3.000 |
| Glycerol monocaprate | 0.100 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 11

| Facial cleansing gel | |
|---|---|
| | % by weight |
| Glyceryl isolaurate | 4.588 |
| Laureth-11-carboxylic acid (90%) | 3.754 |
| Cetearyl isononanoate | 1.773 |
| PEG 150-distearate | 1.000 |
| Cyclomethicone | 3.441 |
| Butylene glycol | 3.128 |
| NaOH | 0.206 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 12

| Body-care gel | |
|---|---|
| | % by weight |
| PEG 20-stearate | 4.800 |
| Glyceryl isostearate | 2.400 |
| Isotridecyl isononanoate | 6.660 |
| PEG 150-distearate | 1.000 |
| Glycerol monocaprate | 0.100 |
| Cyclomethicone | 3.340 |
| Butylene glycol | 3.000 |
| Farnesol | 0.300 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 13

| Aftershave gel | |
|---|---|
| | % by weight |
| Sorbitan isostearate | 2.400 |
| Isotridecyl isononanoate | 1.670 |
| PEG 20-sorbitan monostearate | 4.800 |
| PEG 150-distearate | 1.000 |
| Butylene glycol | 3.000 |
| Glycerol monocaprate | 0.100 |
| Cyclomethicone | 3.330 |
| Farnesol | 0.300 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 14

| Cleansing gel for oily skin | |
|---|---|
| | % by weight |
| Isotridecyl isononanoate | 1.670 |
| PEG 20-sorbitan monooleate | 4.800 |
| Cyclomethicone | 3.330 |
| PEG 150-distearate | 1.000 |
| Butylene glycol | 3.000 |
| Glycerol monooleate | 2.400 |
| Farnesol | 0.300 |
| Glycerol monocaprate | 0.100 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 15

| Aftershave gel | % by weight |
|---|---|
| Isotridecyl isononanoate | 3.311 |
| Glyceryl isostearate | 1.786 |
| Oleth-15 | 5.146 |
| PEG 150-distearate | 1.000 |
| Sorbitol | 2.913 |
| Glycerol monocaprate | 0.194 |
| Cyclomethicone | 6.621 |
| Farnesol | 0.097 |
| Ethanol | 3.883 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 16

| Hair gel | % by weight |
|---|---|
| Glyceryl isostearate | 2.400 |
| Ceteareth-15 | 4.800 |
| PEG 150-distearate | 1.000 |
| Caprylic/capric triglycerides | 3.340 |
| Butylene glycol | 3.000 |
| Glycerol monocaprate | 0.100 |
| Cyclomethicone | 6.660 |
| Farnesol | 0.300 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 17

| Face-care gel | % by weight |
|---|---|
| Glyceryl isostearate | 2.400 |
| PEG 15-cetylstearyl alcohol | 4.800 |
| PEG 150-dioleate | 1.000 |
| Dicaprylyl ether | 5.000 |
| Butylene glycol | 3.000 |
| Glycerol monocaprate | 0.100 |
| Farnesol | 0.300 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 18

| Make-up remover gel | % by weight |
|---|---|
| Diglycerol monoisostearate | 1.840 |
| Ceteareth-15 | 5.300 |
| PEG 150-dioleate | 1.000 |
| Paraffinum liquidum | 5.000 |
| Sorbitol | 3.000 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 19

| Deodorant gel | % by weight |
|---|---|
| Ceteareth-15 | 5.146 |
| Octyl dodecanol | 9.932 |
| PEG 150-dioleate | 1.000 |
| Sorbitol | 2.913 |
| Farnesol | 0.097 |
| Diglycerol monoisostearate | 1.786 |
| Glycerol monocaprate | 0.194 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 20

| Face-care gel | % by weight |
|---|---|
| PEG 6-caprylic acid/capric acid glyceride | 4.800 |
| Isotridecyl isononanoate | 1.670 |
| PEG 230-glyceryl triisostearate | 1.000 |
| Butylene glycol | 3.000 |
| Glycerol monocaprate | 2.400 |
| Cyclomethicone | 3.330 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 21

| | % by weight |
|---|---|
| Glyceryl isostearate | 2.400 |
| Isotridecyl isononanoate | 1.670 |
| Cyclomethicone | 3.330 |
| PEG 450-sorbitol hexaisostearate | 1.000 |
| Butylene glycol | 3.000 |
| PEG 20-glyceryl isostearate | 4.800 |

-continued

| | % by weight |
|---|---|
| Farnesol | 0.300 |
| Glycerol monocaprate | 0.100 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 22

| After-foaming gel | % by weight |
|---|---|
| Glyceryl isolaurate | 4.600 |
| Sodium laureth 1-4-sulphate (25% strength) | 15.000 |
| PEG 150-distearate | 2.000 |
| Cyclomethicone | 3.440 |
| Cetearyl isononanoate | 1.770 |
| Butylene glycol | 3.125 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming. The above mixture is provided with the thickener and four times the amount of a propane/butane 2:7 mixture.

EXAMPLE 23

| Microdispersion gel | % by weight |
|---|---|
| Glyceryl isostearate | 2.400 |
| Ceteth-15 | 4.800 |
| PEG 150-distearate | 1.000 |
| Cetyl palmitate | 4.000 |
| Butylene glycol | 3.000 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 24

| Deodorizing formulation | % by weight |
|---|---|
| Glyceryl isostearate | 1.800 |
| Ceteareth-15 | 5.100 |
| PEG 120-methylglucose dioleate | 1.000 |
| Cyclomethicone | 6.660 |
| Butylene glycol | 2.900 |
| Farnesol | 0.300 |
| Hydrated aluminium chloride | 20.000 |
| Isotridecyl isononanoate | 3.300 |
| Glycerol monocaprate | 0.200 |

-continued

| Deodorizing formulation | % by weight |
|---|---|
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 25

| Deodorizing formulation | % by weight |
|---|---|
| Glyceryl isostearate | 1.800 |
| Ceteareth-15 | 5.100 |
| PEG 160-sorbitan triisostearate | 1.000 |
| Cylcomethicone | 6.660 |
| Sorbitol | 2.900 |
| Farnesol | 0.100 |
| Hydrated aluminium chloride | 7.800 |
| Isotridecyl isononanoate | 3.300 |
| Glycerol monocaprate | 0.200 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

EXAMPLE 26

| Deodorizing formulation | % by weight |
|---|---|
| Glyceryl isostearate | 2.400 |
| Ceteareth-15 | 4.800 |
| Urethane/$C_{1-20}$-alkyl PEG copolymer | 2.000 |
| Cyclomethicone | 6.660 |
| Butylene glycol | 3.000 |
| Farnesol | 0.300 |
| Hydrated aluminium chloride | 20.000 |
| Isotridecyl isononanoate | 3.300 |
| Glycerol monocaprate | 0.100 |
| Perfume, preservative, dyestuffs | q.s. |
| Water | to 100.00 |

The oily phase and the aqueous phase are heated separately to in each case 85–90° C. and combined and the mixture is cooled to room temperature, a transparent to translucent O/W microemulsion gel forming.

What is claimed is:

1. An oil-in-water microemulsion in the form of a gel, said oil-in-water microemulsion comprising:
   a) a continuous aqueous phase;
   b) a discontinuous oil phase in the form of a microemulsion droplets;
   c) a content of less than 20% of the weight of the microemulsion of one or more emulsifiers selected from the group consisting of:
      i) polyethoxylated oil-in-water emulsifiers;
      ii) polypropoxylated oil-in-water emulsifiers; and
      iii) polyethoxylated and polypropoxylated O/W emulsifiers; and wherein said one or more emulsifiers optionally further comprise of water-in-oil emulsifiers; and d) one or more crosslinking substances joining said microemulsion droplets together, wherein the molecules of said crosslinking substances contain at least one hydrophilic region which contains an extension which bridges the distance between at least two microemulsion droplets and at least one hydrophobic region which forms a hydrophobic interaction with at least one of the microemulsion droplets, which is prepared by a process comprising:

a) mixing base components of the aqueous phase, base components of the oil phase, and said emulsifiers to form a mixture thereof; and b) varying at least one parameter selected from the group consisting of temperature and the concentration of emulsifiers, the oil phase and the aqueous phase so that the mixture passes through a phase inversion range between water-in-oil emulsions and oil-in-water emulsions and is brought into a range where the mixture is present as an oil-in-water microemulsion;

wherein said crosslinking substances are added to said mixture at any time during the process.

2. The oil-in-water microemulsion gel according to claim 1, which comprises one or more polyethoxylated oil-in-water emulsifiers.

3. The oil-in-water microemulsion gel according to claim 1, which comprises one or more polypropoxylated oil-in-water emulsifiers.

4. The oil-in-water microemulsion gel according to claim 1, which comprises one or more polyethoxylated and polypropoxylated oil-in-water emulsifiers.

5. The oil-in-water microemulsion gel according to claim 1, which comprises one or more water-in-oil emulsifiers.

6. A cosmetic or dermatological formulation comprising an oil-in-water microemulsion gel according to claim 1.

7. A method of caring for skin and/or hair comprising applying to the skin and/or hair an effective amount therefor of a cosmetic or dermatological formulation according to claim 6.

8. The oil-in-water microemulsion of claim 1, wherein the one or more crosslinking substances are selected from the group consisting of PEG 150-distearate, PEG-150 dioleate, PEG 300-pentaerythrityl tetraisostearate, PEG 120-methylglucose dioleate, PEG 160-sorbitan triisostearate, PEG 450-sorbitol hexaisostearate and PEG 230-glyceryl triisostearate.

9. The oil-in-water microemulsion of claim 1, wherein the amount of said one or more emulsifiers is less than 8.3% by weight based on the total weight of the microemulsion.

* * * * *